(12) United States Patent
Millet

(10) Patent No.: US 12,144,814 B2
(45) Date of Patent: *Nov. 19, 2024

(54) COMPOSITIONS CONTAINING PARAXANTHINE AND BETA-HYDROXYBUTYRATE OR PRECURSOR FOR INCREASING NEUROLOGICAL AND PHYSIOLOGICAL PERFORMANCE

(71) Applicant: AXCESS GLOBAL SCIENCES, LLC, Salt Lake City, UT (US)

(72) Inventor: Gary Millet, Salt Lake City, UT (US)

(73) Assignee: AXCESS GLOBAL SCIENCES, LLC, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/620,393

(22) Filed: Mar. 28, 2024

(65) Prior Publication Data

US 2024/0299398 A1 Sep. 12, 2024

Related U.S. Application Data

(63) Continuation of application No. 18/182,125, filed on Mar. 10, 2023, now Pat. No. 11,969,430.

(51) Int. Cl.
| | | |
|---|---|---|
| *A61K 31/522* | (2006.01) | |
| *A61K 31/047* | (2006.01) | |
| *A61K 31/19* | (2006.01) | |

(52) U.S. Cl.
CPC .......... *A61K 31/522* (2013.01); *A61K 31/047* (2013.01); *A61K 31/19* (2013.01)

(58) Field of Classification Search
CPC ..... A61K 31/522; A61K 31/047; A61K 31/19
See application file for complete search history.

(56) References Cited

U.S. PATENT DOCUMENTS

| | | | |
|---|---|---|---|
| 2,238,149 | A | 4/1941 | Aeckerle |
| 2,976,073 | A | 3/1961 | Russell et al. |
| 4,139,761 | A | 2/1979 | Obrowski |
| 4,224,503 | A | 9/1980 | Gijzel et al. |
| 4,292,499 | A | 9/1981 | Kleinschmidt et al. |
| 4,627,808 | A | 12/1986 | Hughes |
| 4,771,074 | A | 9/1988 | Lammerant et al. |
| 4,969,393 | A | 11/1990 | Mahlich et al. |
| 4,997,976 | A | 3/1991 | Brunengraber et al. |
| 5,093,044 | A | 3/1992 | Wretlind et al. |
| 5,100,677 | A | 3/1992 | Veech |
| 5,116,868 | A | 5/1992 | Chen et al. |
| 5,288,512 | A | 2/1994 | Seiden |
| 5,292,774 | A | 3/1994 | Hiraide et al. |
| 5,654,266 | A | 8/1997 | Chen et al. |
| 5,700,670 | A | 12/1997 | Yamagishi et al. |
| 6,207,856 | B1 | 3/2001 | Veech |
| 6,217,915 | B1 | 4/2001 | Luchansky et al. |
| 6,232,345 | B1 | 5/2001 | Hiraide et al. |
| 6,316,038 | B1 | 11/2001 | Veech |
| 6,323,237 | B1 | 11/2001 | Veech |
| 6,380,244 | B2 | 4/2002 | Martin et al. |
| 6,613,356 | B1 | 9/2003 | Vlahakos |
| 6,706,756 | B1 | 3/2004 | Fitzpatrick et al. |
| 6,835,750 | B1 | 12/2004 | Henderson |
| 7,351,736 | B2 | 4/2008 | Veech |
| 7,807,718 | B2 | 10/2010 | Hashim et al. |
| 7,891,287 | B2 | 2/2011 | Miller |
| 8,101,653 | B2 | 1/2012 | Veech |
| 8,124,589 | B2 | 2/2012 | Henderson |
| 8,344,896 | B2 | 1/2013 | Ozanne |
| 8,426,468 | B2 | 4/2013 | Henderson |
| 8,642,654 | B2 | 2/2014 | Clarke et al. |
| 8,748,400 | B2 | 6/2014 | Henderson |

(Continued)

FOREIGN PATENT DOCUMENTS

| | | |
|---|---|---|
| CA | 2990927 A1 | 7/2018 |
| CN | 86108978 A | 11/1987 |

(Continued)

OTHER PUBLICATIONS

International Preliminary Report on Patentability received for PCT Patent Application No. PCT/US2021/017078, mailed on Aug. 18, 2022, 7 pages.
International Preliminary Report on Patentability received for PCT Patent Application No. PCT/US2021/045186, mailed on Mar. 9, 2023, 7 pages.
International Preliminary Report on Patentability received for PCT Patent Application No. PCT/US2021/050302, mailed on Mar. 2, 2023, 8 pages.
International Preliminary Report on Patentability received for PCT Patent Application No. PCT/US2021/063559, mailed on Jul. 6, 2023, 6 pages.
International Search Report and Written Opinion issued in PCT/US19/48364 dated Nov. 15, 2019.
International Search Report and Written Opinion received for PCT Patent Application No. PCT/US2018/062093, mailed on Feb. 1, 2019, 7 pages.

(Continued)

*Primary Examiner* — Umamaheswari Ramachandran
(74) *Attorney, Agent, or Firm* — Workman Nydegger

(57) ABSTRACT

Disclosed herein are "paraxanthine-BHB" compositions including a combination of: (1) paraxanthine; (2) a ketone body or ketone body precursor, such as beta-hydroxybutyrate (BHB) salt, BHB ester, BHB acid, acetoacetate salt, acetoacetate ester, acetoacetic acid, 1,3-butanediol, medium chain fatty acid, or ester of medium chain fatty acid; and (3) optionally a dietetically or pharmaceutically acceptable carrier. In some embodiments, the composition may include a short chain fatty acid or ester thereof in addition to or instead of the ketone body or ketone body precursor. The composition can provide enhanced cognitive flexibility, improved sustained attention, improved working memory, and neuroprotection in a mammal. In addition to such improved mental acuity characteristics, the composition can also beneficially increase resting energy expenditure (resting metabolic rate), enhancing fat loss principally through ketosis while promoting muscle formation and maintenance, as well as modulating lethargy/lightheadedness when entering a ketogenic state.

20 Claims, 12 Drawing Sheets

(56) References Cited

U.S. PATENT DOCUMENTS

| | | |
|---|---|---|
| 9,138,420 B2 | 9/2015 | D'Agostino et al. |
| 9,211,275 B2 | 12/2015 | Clarke et al. |
| 9,435,566 B2 | 9/2016 | Hill et al. |
| 9,675,577 B2 | 6/2017 | D'Agostino et al. |
| 9,717,767 B2 | 8/2017 | Carpenter et al. |
| 9,795,580 B2 | 10/2017 | Weeber et al. |
| 9,808,481 B2 | 11/2017 | Ritter et al. |
| 9,925,164 B1 | 3/2018 | Hashim |
| 9,957,246 B2 | 5/2018 | Stinchcomb et al. |
| 10,022,409 B2 | 7/2018 | Carpenter et al. |
| 10,051,880 B2 | 8/2018 | Clarke et al. |
| 10,088,197 B2 | 10/2018 | Hamagami et al. |
| 10,245,242 B1 | 4/2019 | Millet |
| 10,245,243 B1 | 4/2019 | Millet |
| 10,292,592 B2 | 5/2019 | Marshall et al. |
| 10,292,952 B2 | 5/2019 | Millet |
| 10,407,331 B2 | 9/2019 | Kamito et al. |
| 10,512,615 B1 | 12/2019 | Millet |
| 10,588,876 B2 | 3/2020 | Millet |
| 10,588,877 B2 | 3/2020 | Arnold |
| 10,596,128 B2 | 3/2020 | Millet |
| 10,596,129 B2 | 3/2020 | Millet |
| 10,596,130 B2 | 3/2020 | Millet |
| 10,596,131 B2 | 3/2020 | Millet |
| 10,660,958 B2 | 5/2020 | Clarke |
| 10,736,861 B2 | 8/2020 | Millet |
| 10,792,269 B2 | 10/2020 | Hashim |
| 10,925,843 B2 | 2/2021 | Millet |
| 10,973,786 B2 | 4/2021 | Millet |
| 10,980,764 B1 | 4/2021 | D'Agostino et al. |
| 10,980,772 B2 | 4/2021 | Millet |
| 11,020,362 B2 | 6/2021 | Millet |
| 11,033,553 B2 | 6/2021 | Millet |
| 11,103,470 B2 | 8/2021 | Millet |
| 11,185,518 B2 | 11/2021 | Millet |
| 11,202,769 B2 | 12/2021 | Millet |
| 11,241,403 B2 | 2/2022 | Millet |
| 11,690,817 B2 | 7/2023 | Millet |
| 2001/0014696 A1 | 8/2001 | Veech |
| 2001/0018866 A1 | 9/2001 | Fischer |
| 2001/0041736 A1 | 11/2001 | Veech |
| 2002/0013339 A1 | 1/2002 | Martin et al. |
| 2003/0022937 A1 | 1/2003 | Veech |
| 2004/0138293 A1 | 7/2004 | Werner et al. |
| 2004/0266872 A1 | 12/2004 | Veech |
| 2005/0129783 A1 | 6/2005 | McCleary et al. |
| 2005/0169968 A1 | 8/2005 | Elmaleh et al. |
| 2006/0165777 A1 | 7/2006 | Solomon et al. |
| 2006/0275253 A1 | 12/2006 | Ushida et al. |
| 2007/0029913 A1 | 2/2007 | Chen |
| 2007/0135376 A1 | 6/2007 | Henderson |
| 2007/0179197 A1 | 8/2007 | Henderson |
| 2008/0058416 A1 | 3/2008 | Greenwood et al. |
| 2008/0287372 A1 | 11/2008 | Henderson |
| 2009/0131475 A1 | 5/2009 | Uesugi et al. |
| 2009/0253781 A1 | 10/2009 | Veech |
| 2009/0325984 A1 | 12/2009 | Costentin et al. |
| 2010/0041751 A1 | 2/2010 | Henderson |
| 2010/0056631 A1 | 3/2010 | Hisamura et al. |
| 2010/0197758 A1 | 8/2010 | Andrews et al. |
| 2010/0210726 A1 | 8/2010 | Kuriyama |
| 2010/0298294 A1 | 11/2010 | Clarke et al. |
| 2011/0237666 A1 | 9/2011 | Clarke et al. |
| 2011/0287114 A1 | 11/2011 | Johnson |
| 2012/0053240 A1 | 3/2012 | Rathmacher et al. |
| 2012/0071548 A1 | 3/2012 | Veech |
| 2012/0171165 A1 | 7/2012 | Buck et al. |
| 2012/0202891 A1 | 8/2012 | Stinchcomb et al. |
| 2013/0079406 A1 | 3/2013 | Veech |
| 2013/0337116 A1 | 12/2013 | Petralia |
| 2014/0256808 A1 | 9/2014 | Henderson |
| 2014/0329893 A1 | 11/2014 | Veech |
| 2014/0350105 A1 | 11/2014 | D'Agostino et al. |
| 2014/0352728 A1 | 12/2014 | Svensson |
| 2015/0065571 A1 | 3/2015 | Clarke et al. |
| 2015/0132280 A1 | 5/2015 | Lopez et al. |
| 2015/0144074 A1 | 5/2015 | Fujimoto et al. |
| 2015/0320809 A1 | 11/2015 | Carpenter et al. |
| 2015/0363750 A1 | 12/2015 | Svensson et al. |
| 2016/0193173 A1 | 7/2016 | Clarke et al. |
| 2016/0256411 A1 | 9/2016 | Aung-Din |
| 2016/0263071 A1 | 9/2016 | Borges et al. |
| 2017/0020844 A1 | 1/2017 | Galinski |
| 2017/0029650 A1 | 2/2017 | Veling et al. |
| 2017/0172969 A1 | 6/2017 | D'Agostino et al. |
| 2017/0258745 A1 | 9/2017 | Millet |
| 2017/0266148 A1 | 9/2017 | D'Agostino et al. |
| 2017/0290792 A1 | 10/2017 | Cavaleri |
| 2017/0296501 A1 | 10/2017 | Lowery et al. |
| 2017/0298339 A1 | 10/2017 | Hanson et al. |
| 2017/0304564 A1 | 10/2017 | Dehaan et al. |
| 2018/0021274 A1 | 1/2018 | Arnold |
| 2018/0021281 A1 | 1/2018 | Berger |
| 2018/0055797 A1 | 3/2018 | Llosa et al. |
| 2018/0057846 A1 | 3/2018 | Llosa et al. |
| 2018/0195096 A1 | 7/2018 | Veech et al. |
| 2018/0214399 A1 | 8/2018 | Spector et al. |
| 2018/0238586 A1 | 8/2018 | Sugatani et al. |
| 2019/0099394 A1 | 4/2019 | Ari et al. |
| 2019/0151267 A1 | 5/2019 | Millet |
| 2019/0167613 A1 | 6/2019 | Millet |
| 2019/0167614 A1 | 6/2019 | Millet |
| 2019/0177673 A1 | 6/2019 | Llosa et al. |
| 2019/0183220 A1 | 6/2019 | Takada |
| 2019/0183820 A1 | 6/2019 | Millet |
| 2019/0183821 A1 | 6/2019 | Millet |
| 2019/0191755 A1 | 6/2019 | Garvey et al. |
| 2019/0209501 A1 | 7/2019 | Tinsley et al. |
| 2019/0262293 A1 | 8/2019 | Millet |
| 2019/0313682 A1 | 10/2019 | Nagel |
| 2019/0321309 A1 | 10/2019 | Millet |
| 2020/0078973 A1 | 3/2020 | Valeze et al. |
| 2020/0140371 A1 | 5/2020 | Verdin et al. |
| 2020/0253909 A1 | 8/2020 | Millet |
| 2020/0268701 A1 | 8/2020 | D'Agostino et al. |
| 2020/0276203 A1 | 9/2020 | Larocca et al. |
| 2021/0095867 A1 | 4/2021 | Gururaja et al. |
| 2021/0106168 A1 | 4/2021 | Cingolani et al. |
| 2021/0205241 A1 | 7/2021 | Millet |
| 2023/0072854 A1 | 3/2023 | Purpura et al. |
| 2023/0115966 A1 | 4/2023 | Wells et al. |

FOREIGN PATENT DOCUMENTS

| | | |
|---|---|---|
| CN | 1256629 A | 6/2000 |
| CN | 1347319 A | 5/2002 |
| CN | 1972698 A | 5/2007 |
| CN | 101674730 A | 3/2010 |
| CN | 101678043 A | 3/2010 |
| CN | 101969769 A | 2/2011 |
| CN | 102164884 A | 8/2011 |
| CN | 104224823 A | 12/2014 |
| CN | 105050594 A | 11/2015 |
| CN | 106038532 A | 10/2016 |
| CN | 106459646 A | 2/2017 |
| CN | 106858066 A | 6/2017 |
| CN | 108253621 A | 7/2018 |
| CN | 109480284 A | 3/2019 |
| DE | 102017210992 A1 | 1/2019 |
| EP | 0008700 A1 | 3/1980 |
| EP | 1112711 A1 | 7/2001 |
| EP | 1178748 A1 | 2/2002 |
| EP | 1827412 A1 | 9/2007 |
| EP | 1915144 A2 | 4/2008 |
| EP | 2283834 A2 | 2/2011 |
| EP | 2976073 A1 | 1/2016 |
| EP | 3094321 A1 | 11/2016 |
| EP | 3366173 A2 | 8/2018 |
| EP | 3446045 A1 | 2/2019 |
| FR | 2997302 A1 | 5/2014 |
| GB | 2391493 A | 2/2004 |
| ID | 201701176 | 2/2017 |
| JP | 11-060434 A | 3/1999 |
| JP | 2002-521330 A | 7/2002 |

(56) References Cited

FOREIGN PATENT DOCUMENTS

| | | | |
|---|---|---|---|
| JP | 2004-035417 A | 2/2004 |
| JP | 2015-042644 A | 3/2015 |
| JP | 2015-514104 A | 5/2015 |
| JP | 2015-102323 A | 6/2015 |
| JP | 2016-514725 A | 5/2016 |
| JP | 2016-121128 A | 7/2016 |
| JP | 2017-046688 A | 3/2017 |
| JP | 2020-502652 A | 1/2020 |
| JP | 2020-527583 A | 9/2020 |
| JP | 2021-504476 A | 2/2021 |
| JP | 2021-506294 A | 2/2021 |
| RU | 2345546 C2 | 2/2009 |
| WO | 87/03808 A1 | 7/1987 |
| WO | 98/41200 A1 | 9/1998 |
| WO | 00/69315 A1 | 11/2000 |
| WO | 03/70823 A2 | 8/2003 |
| WO | 2005/107724 A1 | 11/2005 |
| WO | 2006/061624 A1 | 6/2006 |
| WO | 2007/115282 A2 | 10/2007 |
| WO | 2008/005818 A1 | 1/2008 |
| WO | 2008/021394 A2 | 2/2008 |
| WO | 2008/024408 A2 | 2/2008 |
| WO | 2009/089144 A1 | 7/2009 |
| WO | 2010/021766 A1 | 2/2010 |
| WO | 2011/101171 A1 | 8/2011 |
| WO | 2013/057506 A1 | 4/2013 |
| WO | 2013/150153 A1 | 10/2013 |
| WO | 2014/153416 A1 | 9/2014 |
| WO | 2015/071811 A1 | 5/2015 |
| WO | 2015/156865 A1 | 10/2015 |
| WO | 2016/123229 A1 | 8/2016 |
| WO | 2016/149687 A1 | 9/2016 |
| WO | 2017/156446 A1 | 9/2017 |
| WO | 2017/165443 A1 | 9/2017 |
| WO | 2017/165445 A1 | 9/2017 |
| WO | 2017/182664 A1 | 10/2017 |
| WO | 2017/208217 A2 | 12/2017 |
| WO | 2018/055388 A1 | 3/2018 |
| WO | 2018/089863 A1 | 5/2018 |
| WO | 2018/114309 A1 | 6/2018 |
| WO | 2018/175879 A1 | 9/2018 |
| WO | 2018/187324 A1 | 10/2018 |
| WO | 2018/187852 A1 | 10/2018 |
| WO | 2019/018683 A1 | 1/2019 |
| WO | 2019/099531 A1 | 5/2019 |
| WO | 2019/108683 A1 | 6/2019 |
| WO | 2019/204148 A1 | 10/2019 |
| WO | 2019/237152 A1 | 12/2019 |
| WO | 2022/232469 A1 | 11/2022 |

OTHER PUBLICATIONS

International Search Report and Written Opinion received for PCT Patent Application No. PCT/US20/017555, mailed on May 4, 2020, 8 pages.
International Search Report and Written Opinion received for PCT Patent Application No. PCT/US20/37289, mailed on Sep. 30, 2020, 8 pages.
International Search Report and Written Opinion received for PCT Patent Application No. PCT/US2014/031237, mailed on Jul. 15, 2014, 11 pages.
International Search Report and Written Opinion received for PCT Patent Application No. PCT/US2017/021886, mailed on Jun. 1, 2017, 15 pages.
International Search Report and Written Opinion received for PCT Patent Application No. PCT/US2018/062096, mailed on Feb. 11, 2019, 13 pages.
International Search Report and Written Opinion received for PCT Patent Application No. PCT/US2019/027214, mailed on Jun. 25, 2019, 14 pages.
International Search Report and Written Opinion received for PCT Patent Application No. PCT/US2019/048357, mailed on Nov. 18, 2019, 13 pages.
International Search Report and Written Opinion received for PCT Patent Application No. PCT/US2020/016952, mailed on Apr. 22, 2020, 9 pages.
International Search Report and Written Opinion received for PCT Patent Application No. PCT/US2020/017552, mailed on May 4, 2020, 9 pages.
International Search Report and Written Opinion received for PCT Patent Application No. PCT/US2020/017556, mailed on May 4, 2020, 12 pages.
International Search Report and Written Opinion received for PCT Patent Application No. PCT/US2020/033159, mailed on Aug. 12, 2020, 9 pages.
International Search Report and Written Opinion received for PCT Patent Application No. PCT/US2021/063559, mailed on Mar. 18, 2022, 9 pages.
International Search Report and Written Opinion received for PCT Patent Application No. PCT/US21/045186, mailed on Nov. 22, 2021, 10 pages.
International Search Report and Written Opinion received for PCT Patent Application No. PCT/US21/17078, mailed on Apr. 23, 2021, 9 pages.
International Search Report and Written Opinion received for PCT Patent Application No. PCT/US24/17857, mailed on May 10, 2024, 10 pages.
Invitation to Respond to Written Opinion issued by the Intellectual Property Office of Singapore dated Dec. 28, 2016 for corresponding Singapore Patent Application No. 11201506780R.
It Really is in Your Blood: Glucose to Ketone Ratios. Greymadder, Sep. 15, 2014. Downloaded Apr. 1, 2015. http://greymadder.net/2014/09/15/it-really-is-in-your-blood-glucose-to-ketone-ratios/.
James, "Optical Purity and Enantiomeric Excess" at https://www.master organicchemistry.com/2017/02/24/optical-purity-and-enantiomeric-excess/. (Retrieved from the internet Nov. 6, 2018) (Year: 2018).
John C Newman et al: "beta-Hydroxybutyrate: A Signaling Metabolite", Annual Review of Nutrition, vol. 37, Aug. 21, 2017 (Aug. 21, 2017), pp. 51-76, XP055771586.
Karppanen, H., et al, "Why and how to implement sodium, potassium, calcium, and magnesium changes in food items and diets?" J. Human Hypertension (2005), vol. 19, pp. S10-S19.
Kaster M.P. et al, "Caffeine acts through neuronal adenosine A2A receptors to prevent mood and memory dysfunction triggered by chronic stress", Proceedings of the National Academy of Sciences, vol. 112, No. 25, Jun. 8, 2015, pp. 7833-7838.
Kesl, et al., "Effects of exogenous ketone supplementation on blood ketone, glucose, triglyceride, and lipoprotein levels in Sprague-Dawley rats", Nutrition & Metabolism (2016).
Kim Do Young et al., "Ketone bodies are protective against oxidative stress in neocortical neurons," Journal of Neurochemistry, vol. 101, Issue 5, Jun. 1, 2007, pp. 1316-1326.
Kirsch, Jr et al. "Butanediol Induced Ketosis Increases Tolerance to Hypoxia in the Mouse." Stroke. 1980. vol. 11, No. 5, pp. 506-513.
Kossoff, Eric H. et al. "Optimal Clinical Management of Children Receiving the Ketogenic Diet: Recommendations of the International Ketogenic Diet Study Group." Epilepsia, Feb. 2009;50(2):304-17. Epub Sep. 23, 2008.
Krotkiewski, "Value of VLCD Supplementation with Medium Chain Triglycerides", Int J Obes Relat Metab Disord, Sep. 2001, 25(9), pp. 1393-1400.
Lang Chaochun, "Healthy fitness and exercise prescription", Nov. 30, 2013, p. 201.
Lile et al. Drug Alcohol Depend. 2012, 122 (1-2), 61-69.
Lonza, Duocap Capsules, Feb. 16, 2018, https ://web .archive.org/web/20180216001656/https://www.capsugel.com/consumer-health-nutrition-products/duocap-capsules (Year: 2018).
Luis Villasenor, "Supplements and Ketogenic Diets—Facts and Myths", Retrieved from https://www.ketogains.com/2015/09/supplements-and-ketogenic-diets-facts-and-myths/, Sep. 18, 2015, pp. 15.
Lytra. G. et al., "Distribution and Organoleptic Impact of Ethyl 3-Hydroxybutanoate Enantiomers in Wine," J. Agric. Food Chem, vol. 63, Issue 48, 2015, pp. 10484-10491.

(56) References Cited

OTHER PUBLICATIONS

Maalouf Met Al., "Ketones inhibit mitochondrial production of reactive oxygen species production following glutamate excitotoxicity by increasing NADH oxidation," Neuroscience, New York, NY, US, vol. 145, Issue 1, Mar. 2, 2007, pp. 256-264.
Maalouf Met Al., "The neuroprotective properties of calorie restriction, the ketogenic diet, and ketone bodies," Brain Research Reviews, Elsevier, NL, vol. 59, No. 2, Mar. 1, 2009, pp. 293-315.
Maguire et al., "Gut dysbiosis, leaky gut, and intestinal epithelial proliferation in neurological disorders: towards the development of a new therapeutic using amino acids, prebiotics, probiotics, and postbiotics", Rev Neurosci . Jan. 28, 2019, vol. 30, No. 2, pp. 179-201.
Malo, M. S. et al., Intestinal alkaline phosphatase preserves the normal homeostasis of gut microbiota, 2010, Gut, 59, 1476-1484 (Year: 2010).
Mangels D.R. et al, "Catechins as Potential Mediators of Cardiovascular Health", Translational Sciences, vol. 37, No. 5, May 1, 2017, pp. 757-763.
Murray, Andrew J., et al. "Novel ketone diet enhances physical and cognitive performance", The FASEB Journal, No. 30 Dec. 2016.
National Center for Biotechnology Information. PubChem Compound Summary for CID 441, 3-Hydroxybutyric acid, https://pubchem.ncbi.nlm.nih.gov/compound/3-Hydroxybutyric-acid. (Year: 2005).
Non-Final Rejection Mailed on Sep. 9, 2020 for U.S. Appl. No. 16/783,956.
Nova Max Plus Glucose and Ketone Testing with One Monitor. Downloaded Apr. 1, 2015. http://www.novacares.com/nova-max-plus/.
O'Mailey et al, Appl. Physiol. Nutr. Metab. 42: 1031-1035 (2017) Published at www.NRCRESEARCHPRESS.com/APNM on Jul. 27, 2017.
O'Meara, Cyndi, Changing Habits, Ketosis—Can we achieve it in a pill?, https://changinghabits.com.au/ketosis-can-we-achieve-it-in-a-pill/, 12 pages, (Jan. 13, 2017).
Office Action received for European Patent Application No. 19788264.0, mailed on Mar. 13, 2024, 5 pages.
Office Action received for European Patent Application No. 20805593.9, mailed on Dec. 22, 2023, 7 pages.
3-Hydroxybutyric acid; PubChem, 2023 (Year: 2023).
A New Toy Measuring Blood Ketones. Diet Doctor, Aug. 21, 2012. Dowloaded Apr. 1, 2015. http://www.dietdoctor.com/a-new-toy-measuring-blood-ketoones.
Amazon, "Perfect Keto Perform Pre Workout Powder—Burn Fat for Fuel Energy Supplement Drink Mix for Men and Women—Keto Friendly with Ketone Salts, BCAA, Nitric Oxide & MCT", Sep. 25, 2017 entire document especially p. 1 Retrieved from https://www.amazon.com/Perfect-Keto-Perform-PreworkoutSupplement/dp/B0751379Q9/ref=sr_1_9?dchild=1&keywords=ketone+pre+workout&qid=1597938465&sr=8-9.
Anonymous: "Blue Lemon Ice Advanced Formula", Mintel, Database accession No. 4315637, 2016, pp. 3.
Anonymous: "Strawberry Pineapple Flavour Pre-Exertion Performance Optimizer", Mintel, Database accession No. 5661617, 2018, pp. 4.
Arendash et al. "Caffeine and Coffee as Therapeutics Against Alzheimer's Disease", Journal of Alzheimer's Disease 20, 2010, S117-S126.
Arnold, Instant Ketosis?, (2013), Aug. 4, 2013 (retrieved on Apr. 21, 2017), p. 1-3. Retrieved from the internet; URL: <http://patrickarnoldblog.com/instant-ketosis/. (Year: 2013).
Bala et al. Drug Invention Today. Jun. 1, 2018;10(6), 929-931.
Bastin et al., "Salt Slection and Optimisation Procedures for Pharmaceutical New Chemical Entities", American Chemical Society and the Royal Society of Chemistry, vol. 4, No. 5, 2000, pp. 427-435.
Blazquez et al. Journal of Neurochemistry, 1999, vol. 72 No. 4, pp. 1759-1768. (Year: 1999).

Budin. N. et al., "Efficient synthesis of the ketone body ester (R)-3-hydroxybutyryl-(R)-3-hydroxybutyrate and its (S, S) enantiomer," Bioorganic Chemistry, vol. 80, Oct. 2018, pp. 560-564.
Clarke, et al., Kinetics, safety and tolerability of (R)-3-hydroxybutyl (R)-3-hydroxybutyrate in healthy adult subjects. Regul Toxicol Pharmacol. Aug. 2012; 63(3):401-8.
Craciun, S. et al. Microbial conversion of choline to trimethylamine requires a glycyl radical enzyme, 2012, PNAS, 109(52): 21307-21312 (Year: 2012).
Cresci, G. et al., Lactobacillus GG and Tributyrin Supplementation Reduce Antibiotic-Induced Intestinal Injury, 2013, Journal of Parenteral and Enteral Nutrition, 37(6), 1-20 (Year: 2013).
Daniells, Stephen, 'This is caffeine-evolved': Ingenious Ingredients co-founder talks up potential of paraxanthine, Nov. 3, 2021, 2 pages, retrieved from https://www.nutraingredients-usa.com/Article/2021/11/03/This-is-caffeine-evolved-Ingenious-Ingredients-co-founder-talks-up-potential-of-paraxanthine accessed Feb. 7, 2023.
Database GNPD Mintel, Sep. 29, 2016, anonymous, "Blue Lemon Ice Advanced Formula", XP093048090, Database accession No. 4315637, pp. 3.
Dietary Guidelines Recommendations at https://health.gov/our-work/food-nutrition/2015-2020-dietary-guidelines/guidelines/ appendix-7/ (2010) (retrieved from the internet Oct. 20, 2020) (Year: 2010).
Dolson, Laura. How to Test Your Blood for Ketones. Downloaded Apr. 1, 2015. http://lowcarbdiets.about.com/od/KetogenicDiets/a/How-to-Test-Blood-For-Ketones.htm.
European Search Report received for EP Patent Application No. 20755289.4, mailed on Oct. 11, 2022, 7 pages.
European Search Report received for EP Patent Application No. 20755994.9, mailed on Sep. 21, 2022, 6 pages.
European Search Report received for EP Patent Application No. 20805593.9, mailed on Dec. 16, 2022, 9 pages.
European Search Report received for EP Patent Application No. 21750261.6, mailed on Feb. 2, 2024, 10 pages.
Extended European Search Report pursuant to Rule 62 EPC (EPO Form 1507S) issued on Jan. 24, 2017 for corresponding European Patent Application No. 14770025.6.
Extended European Search Report received for EP Patent Application No. 19788264.0, mailed on Dec. 20, 2021, 11 pages.
Extended European Search Report received for EP Patent Application No. 20755770.3, mailed on Sep. 1, 2022, 7 pages.
First Examination Report for New Zealand Patent Application No. 711433 issued by the New Zealand Intellectual Property Office dated Mar. 10, 2016.
First Office Action issued by the Chinese State Intellectual Property Office on Nov. 4, 2016 for corresponding Chinese Patent Application No. 201480016818.0.
Grootaert, C. Comparison of prebiotic effects of arabinoxylan oligosaccharides and inulin in a simulator of the human intestinal microbial ecosystem, 2009, FEMS Microbiology Ecology, 69: 231-242 (Year: 2009).
Haces M L et al: "Antioxidant capacity contributes to protection of ketone bodies against oxidative damage induced during hypoglycemic conditions", Experimental Neurology, Elsevier, Amsterdam, NL, vol. 211, No. 1, May 1, 2008 (May 1, 2008), pp. 85-96.
Hashim, Sami A., et al., "Ketone body therapy: from the ketogenic diet to the oral administration of ketone ester", Journal of Lipid Research, vol. 55, 2014.
Haywood A, Glass BD. Pharmaceutical excipients—where do we begin? Australian Prescriber. 2011; 34: 112-114.
Henderson, Samuel T. "Ketone Bodies as a Therapeutic for Alzheimer's Disease." Neurotherapeutics. Jul. 2008; 5(3):470-80.
Holscher, H. Dietary fiber and prebiotics and the gastrointestinal microbiota, 2017, Gut Microbes, 8(2): 172-184 (Year: 2017).
Holtzman et al., "Role of adenosine receptors in caffeine tolerance", J. Pharmacol. Exp. Ther., 1991 ;256(1 ):62-68.
Huang Dexiang et al., "Clinical Intravenous Nutrition", Shanghai Medical University Press Jan. 31, 1994, pp. 121-124.
Huang Dexiang, "Clinical Intravenous Nutrition", Shanghai Medical University Press, Apr. 17, 2023, pp. 1-5.

(56) References Cited

OTHER PUBLICATIONS

Ichim, T. et al., Experimental support for the effects of a probiotic/digestive enzyme supplement on serum cholesterol concentrations and the intestinal microbiome, 2016, Journal of Translational Medicine, 14(184), 1-9 (Year 2016).
International Preliminary Report on Patentability received for PCT Patent Application No. PCT/US2020/016952, mailed on Aug. 26, 2021, 7 pages.
International Preliminary Report on Patentability received for PCT Patent Application No. PCT/US20/37289, mailed on Dec. 30, 2021, 6 pages.
International Preliminary Report on Patentability received for PCT Patent Application No. PCT/US2014/031237, mailed on Oct. 1, 2015, 8 pages.
International Preliminary Report on Patentability received for PCT Patent Application No. PCT/US2017/021886, mailed on Sep. 20, 2018, 9 pages.
International Preliminary Report on Patentability received for PCT Patent Application No. PCT/US2018/062093, mailed on Jun. 4, 2020, 6 pages.
International Preliminary Report on Patentability received for PCT Patent Application No. PCT/US2018/062096, mailed on Jul. 2, 2020, 8 pages.
International Preliminary Report on Patentability received for PCT Patent Application No. PCT/US2019/027214, mailed on Oct. 29, 2020, 09 pages.
International Preliminary Report on Patentability received for PCT Patent Application No. PCT/US2019/048357, mailed on Mar. 11, 2021, 08 pages.
International Preliminary Report on Patentability received for PCT Patent Application No. PCT/US2019/048364, mailed on Mar. 11, 2021, 7 pages.
International Preliminary Report on Patentability received for PCT Patent Application No. PCT/US2020/017552, mailed on Aug. 26, 2021, 7 pages.
International Preliminary Report on Patentability received for PCT Patent Application No. PCT/US2020/017555, mailed on Aug. 26, 2021, 7 pages.
International Preliminary Report on Patentability received for PCT Patent Application No. PCT/US2020/017556, mailed on Aug. 26, 2021, 7 pages.
International Preliminary Report on Patentability received for PCT Patent Application No. PCT/US2020/033159, mailed on Nov. 25, 2021, 6 pages.
Paraxanthine-Pubchem—2023 (Year: 2023).
Parker, Steve, "Ketogenic Mediterraanean Diet: Version 2.3," Nov. 23, 2010, pp. 1-3. (Year: 2010).
Pete J Cox et al., "Acute nutritional ketosis: implications for exercise performance and metabolism," Extreme Physiology & Medicine, vol. 3, Issue 1, Dec. 1, 2014, pp. 1-9.
Precision Xtra vs. NovaMax Plus: Ketone Meter Evaluation. Jimmy Moore's Livin' La Vida Low Garb Blog. Downloaded Apr. 1, 2015. http://livinlavidalowcarb.com/blog/precision-xtra-vs-novamax-plus-ketone-meter-evaluation/15918.
Pubchem, "Acetoacetic acid" Electronic Resource: https://pubchem.ncbi.nim.nih.gov/compound/Acetoacetic-acid, Retrieved on Sep. 3, 2019.
Rho et al. "Acetoacetate, Acetone, and Dibenzylamine (A Contaminant in L-(+)-Beta-Hydroxybutyrate) Exhibit Direct Anticonvulsant Actions in Vivo", Epilepsia, Raven Press Ltd, New York, US, vol. 43, No. 4, Apr. 1, 2002 (Apr. 1, 2002), pp. 358-361.
Rich A.J., "Ketone Bodies as Substrates," Proceedings of the Nutrition Society (1990), vol. 49, 361-373.
Robson et al. Expert Opin. Drug Saf. (2011), vol. 10, pp. 675-685 (Year: 2011).
Roeder, Lois M., et al. The Effects of Ketone Bodies, Bicarbonate, and Calcium on Hepatic Mitochondrial Ketogenesis. Archives of Biochemistry and Biophysics, vol. 217, No. 2, Sep. pp. 460-467, 1982.
Sajewicz et al. In Journal of Liquid Chromatography & Related Technologies, 33:1047-1057 (2010) (Year: 2010).
Sanchez, J. I. et al. Arabinoxylan-oligosaccharides (AXOS) affect the protein/carbohydrate fermentation balance and microbial population dynamics of the Simulator of Human Intestinal Microbial Ecosystem, 2009, Microbial Biotechnology, 2(1): 101-113 (Year: 2009).
Sara, How do you know which product is right for you? How to choose exogenous ketones, https://ketosupplements.co.uk/how-to-choose-exogenous-ketones/, 10 pages, (Sep. 25, 2017).
Search Report and Written Opinion issued by the Intellectual Property Office of Singapore on Apr. 18, 2016 for corresponding Singapore Application No. 11201506780R.
Serum Ketones Test. MedlinePlus Medical Encyclopedia. Downloaded Apr. 1, 2015. http://www.nlm.nih.gov/medlineplus/ency/article/003498.htm.
Shigeno et al. in Biosci. Biotech. Biochem., 56(2), 320-323 (1992) (Year: 1992).
Short, Jay, Effects of A Ketone/Caffeine Supplement On Cycling and Cognitive Performance, Master's thesis, Ohio State University, 61 pages, (Jan. 1, 2017).
Slavin, J. Fiber and Prebiotics: Mechanisms and Health Benefits, 2013, Nutrients, 5: 1417-1425 (Year: 2013).
Sorensen et al. ("Simultaneous determination of β-hydroxybutyrate and β-hydroxy-β-methylbutyrate in human whole blood using hydrophilic interaction liquid chromatography electrospray tandem mass spectrometry", Clinical Biochemistry, 2013, vol. 46, pp. 1877-1883) (Year: 2013).
Stubbs et al., "On the Metabolism of Exogenous Ketones in Humans", frontiers in Physiology, vol. 8, 2017, 13 pages.
Tanaka, J., et al., "Significance of Blood Ketone Body Ration as an indicator of Hepatic Cellular Energy Status in Jaundiced Rabbits", Gastroenterology, 1979, vol. 76, No. 4, pp. 691-696.
The Medical Republic, 2018, Sustained Release Sodium Butyrate Supplement Now Available to Support Management of GI Disorders, https://medicalrepublic.com.au/sustained-release-sodium-butyrate-supplement-now-available-support-management-gi-disorders/15791; newly cited (Year: 2018).
Tisdale, "Reduction of weight loss and tumour size in a cachexia model by a high fat diet", British Journal of Cancer, Jul. 1987, vol. 56, p. 39-43.
Tsai et al., "Stereoselective effects of 3-hydroxybutyrate on glucose utilization of rat cardiomyocytes" life Sciences 78(2006) pp. 1385-1391.
Vandenberghe et al. in Can. J. Physiol. Pharmacol. 95:455-458 (2017) (Published at www.nrcresearchpress com/cjpp on Nov. 25, 2016). (Year: 2016).
Veech, "The Therapeutic Implications of Ketone Bodies: The Effects of Ketone Bodies in Pathological Conditions: Ketosis, Ketogenic Diet, Redox States, Insulin Resistance, and Mitochondrial Metabolism", Prostaglandins Leukot Essent Fatty Acids, Mar. 2004, 70(3), pp. 309-319.
Veech, et al., "Ketone Bodies Mimic the Life Span Extending Properties of Caloric Restriction", IUBMB Life Feb. 8, 2017.
Veech, Richard L. "The Therapeutic Implications of Ketone Bodies: The Effects of Ketone Bodies in Pathological Conditions: Ketosis, Ketogenic Diet, Redox States, Insulin Resistance, and Mitochondrial Metabolism." Prostaglandins Leukot Essent Fatty Acids. Mar. 2004;70(3):309-19.
Vorgerd, M. And J. Zange. Treatment of glycogenosys type V (McArdle disease) with creatine and ketogenic diet with clinical scores and with 31P-MRS on working leg muscle. Acta Myologica, 2007; XXVI; pp. 61-63.
Walton, G. et al. A randomised, double-blind, placebo controlled cross-over study to determine the gastrointestinal effects of consumption of arabinoxylan-oligosaccharides enriched bread in healthy volunteers, 2012, Nutrition Journal, 11(36): 1-11 (Year: 2012).
WO2009045481, Pan et al. Published Apr. 9, 2009 Listed in this section as citation type "foreign" does not allow for any appropriate country code for "WO" documents.
Wu et al., "Medium-Chain Triglycerides in Infant Formulas and Their Relation to Plasma Ketone Body Concentrations," Pediatric Research, vol. 20, No. 4, (1986), pp. 338-341.

(56) References Cited

OTHER PUBLICATIONS

Yang Y. et al., Role of Adherent-Invasive *Escherichia coli* in Inflammatory Bowl Disease, Letters in Biotechnology, No. 06, Nov. 30, 2016.
Yang Yue et al., Research on sarcopemc obesity, Chinese Journal of Modern Medicine, vol. 20, No., 3, Mar. 25, 2018, pp. 98-101.
Yang Zeyi, "Biochemistry of sports nutrition scientific research progress", Mar. 31, 2004, vol. 23, No. 2, pp. 158-165.
Zaleski, A. et al., Butyric acid in irritable bowel syndrome, 2013, Prz Gastroenterol, 8(6), 350-353 (Year: 2013).
Zare et al., "Wake-Promoting Agents, Insights into Clinical Use and Molecular Perspectives," Journal of Advanced Medical Sciences and Applied Technologies (JAMSAT), vol. 2, 2016, pp. 129-140.
Zeng Jing et al., "B-hydroxy-3-methyl—The clinical effects and mechanism", vol. 2, No. 2, Jun. 9, 2015, pp. 57-62.

COMPOSITIONS CONTAINING PARAXANTHINE AND BETA-HYDROXYBUTYRATE OR PRECURSOR FOR INCREASING NEUROLOGICAL AND PHYSIOLOGICAL PERFORMANCE

CROSS REFERENCE TO RELATED APPLICATION

This application is a continuation of U.S. application Ser. No. 18/182,125, filed Mar. 10, 2023, now U.S. Pat. No. 11,969,430, which is incorporated by reference in its entirety.

BACKGROUND

Energy drinks and similar caffeinated drinks are beverages used by consumers to promote wakefulness, maintain alertness, and enhance mood and cognition. Typical gas station energy drinks commonly include high fractions of caffeine and sugar. Some may also include vitamins, electrolytes, or amino acids.

Despite widespread use, there are several health concerns surrounding consumption of such caffeinated drinks, particularly surrounding their effects on the cardiovascular system. Such caffeinated energy drinks have been shown to increase heart rate, increase blood pressure, and even thicken the blood. Such drinks may also affect the brain in undesirable ways, such as by raising stress levels and inducing anxiety, insomnia, gastrointestinal irritation, muscle twitching, and periods of prolonged restlessness.

Such drinks are also associated with high levels of fatigue, irritability, and sub-optimal cognition following the initial boost after consumption. This energy "crash" can be long lasting and unpleasant. As the stimulating effects of the caffeine wear off, levels of adrenaline, dopamine, and acetylcholine begin to drop, and blood sugar levels may swing erratically, often leaving the user feeling more fatigued, irritable, and unfocused than before consuming the drink. The user's adenosine levels may continue to rise after dosing with caffeine. When caffeine is no longer available to block adenosine receptors, the rapid flood of built-up adenosine to the receptors can contribute to the perceived crash.

To date, popular gas station caffeinated energy drinks have generally failed to improve the overall quality of life and well-being of users. Rather, such energy drinks provide a short-lived boost in perceived alertness but with a subsequent crash that often tends to be so uncomfortable as to negate the benefits and place consumption of such drinks as a net negative experience. When used to stay awake while driving, such drinks can cause high levels of stress and possibly contribute to "road rage". For long haul drives, the mental and/or physical "crash" by the user is potentially harmful or even fatal if it leads to a highway crash.

Accordingly, there is an ongoing need for compositions that are capable of promoting a natural and sustained feeling of wakefulness, maintaining a natural feeling of alertness without jitteriness or racing heartrate, increasing concentration, mental clarity and working memory, enhancing mood, and/or enhancing cognitive flexibility without the typical energy crash, and without damaging the long-term physiological or mental health of the user.

Ketone bodies are produced from fat and are an alternative caloric source to glucose, particularly when glucose is not available. During periods of fasting, extreme exercise, and/or low carbohydrate consumption, glucose and glycogen stores in the body are rapidly used and can become quickly depleted. Failure to replenish glucose stores as they become depleted causes the body to metabolically shift to using ketone bodies as primary caloric energy. This metabolic state is called "ketosis".

Ketone bodies can be used by cells of the body as a fuel in addition to or instead of glucose to satisfy the body's energy needs, including the brain and heart. During prolonged fasting blood ketone levels can increase to 2-3 mmol/L or more. It is conventionally understood that when blood ketones rise above 0.5 mmol/L, the heart, brain, and peripheral tissues are using ketone bodies (e.g., beta-hydroxybutyrate and acetoacetate) as the primary caloric energy source. This condition is referred to as "ketosis". At between 1.0 mmol/L and 3.0 mmol/L, this condition is referred to as "nutritional ketosis."

Upon transitioning into ketosis, or in other words, during ketogenic metabolism in the liver, the body uses dietary and stored body fats as a primary energy source. Consequently, once in ketosis, one can induce loss of body fat by controlling dietary fat and maintaining low carbohydrate intake to maintain a ketogenic metabolic state. While in ketosis, the body is essentially burning fat as its primary fuel.

The metabolism of ketone bodies is associated with several beneficial effects. However, despite the many health advantages of pursuing a ketogenic diet or lifestyle and maintaining a state of nutritional ketosis, there remain significant barriers to pursuing and maintaining a ketogenic state. One of these barriers is the difficulty of transitioning into a ketogenic state. The fastest endogenous way to entering ketosis is to adopt a catabolic state through depleting glucose stores in the body through fasting combined with high intensity exercise. This will deplete the body's limited glucose and glycogen stores. This is physically and emotionally demanding and is extremely challenging even for the most motivated and disciplined.

In addition, the transition into ketosis is often accompanied by hypoglycemia, which can cause lethargy and lightheadedness in many, resulting in an uncomfortable physiological and mental state commonly referred to as "low-carb flu" or "keto flu." Many people also experience a downregulation in their metabolism as the body goes into an "energy-saving" mode. Some suggest that these transitory symptoms may last as long as two to three weeks. During this transition period, if any meal or snack consisting of carbohydrates over the restrictive amount is consumed, there is a rapid termination of ketogenesis, causing the body to exit ketosis and shift back to glucose as its primary fuel. At this point, the difficult transition into ketosis must begin anew. Thus, despite the potential of a ketogenic diet for weight loss and other health benefits, serious limitations continue to hinder the full realization of its potential.

It would be beneficial to provide a dietary supplement composition that could address at least some of these unpleasant affects associated with entering a ketogenic state (e.g., minimizing or preventing the lethargy and/or lightheadedness, minimizing or preventing the typical downregulation of metabolic rate, etc.).

SUMMARY

Disclosed herein are compositions that include a combination of: (1) paraxanthine; (2) beta-hydroxybutyrate ("BHB"); and (3) optionally a dietetically or pharmaceutically acceptable carrier. For case of reference, such combination compositions may be referred to herein as "Paraxanthine-BHB", or "BHB-Paraxanthine". In some embodiments, a BHB precursor such as 1,3-butanediol can be used in addition to or instead of BHB.

Also disclosed herein are methods of using such compositions for neuroprotection, improved cognitive flexibility, improved working memory, reduced oxidative stress, minimizing or preventing lethargy or lightheadedness (e.g., low carb flu or keto flu) associated with entering a state of nutritional ketosis, minimizing or preventing downregulation of metabolic rate typically associated with entering a state of nutritional ketosis, or other benefits. It has been found that combining paraxanthine with BHB results in a synergistic enhancement to one or more such functional characteristics within the user. For example, paraxanthine provides benefits of improved cognitive flexibility, the ability to achieve sustained attention, improved working memory, and enhanced inhibitory control. When paired with BHB, these benefits are synergistically enhanced, beyond any such benefit provided by either paraxanthine or BHB alone, and additional benefits are also provided, such as limiting effects of hypoglycemia upon entering a ketogenic state, maintaining or even increasing metabolic rate upon entering a ketogenic state, etc.

Such combinations also provide for improved results over a comparative combination of caffeine plus BHB, as the paraxanthine plus BHB does not exhibit the same undesirable secondary effects (subsequent crash, jitters, racing heartrate, increased incidence of mental errors, etc.) associated with caffeine. For example, by providing paraxanthine directly, rather than caffeine, in combination with BHB, the theophylline and theobromine that would metabolically result from use of caffeine are largely if not wholly eliminated, which components are believed to be at least partially responsible for the undesirable secondary effects associated with caffeine use (e.g., jitters, racing heart, increased mental errors, etc.). In addition, by providing BHB in such an environment (i.e., with paraxanthine, and in the general absence of theophylline and theobromine), the BHB, which is a ketone body capable of providing caloric energy, is able to more effectively be used, enhancing benefits such as improved cognitive flexibility, improved sustained attention, improved working memory, and enhanced inhibitory control. The combined use of paraxanthine and BHB also advantageously minimizes lethargy and lightheadedness associated with hypoglycemia upon entering a ketogenic state, as well as the typical downregulation of metabolic rate that occurs upon entering a ketogenic state.

The combination of paraxanthine and BHB is also beneficial because it allows a lower dosage of paraxanthine to be provided to a user, when delivered with the BHB, while still providing a similar level of benefits associated with paraxanthine use. In other words, while a given dosage of paraxanthine, when administered by itself, may be required to provide particular benefits relative to improved cognitive flexibility, improved sustained attention, improved working memory, and enhanced inhibitory control, a lower dosage of paraxanthine may be sufficient to provide similar benefits when combined with BHB. This is advantageous in reducing cost of a supplement capable of providing a given benefit. Alternatively, greater benefits can be provided at similar cost (if the paraxanthine dose is maintained, while also providing BHB).

The BHB ketone body component provides an exogenous source of ketone bodies that can be utilized by the body for energy without significantly causing the user to "break" a fast (e.g., will not cause a significant increase in blood insulin levels) and thereby lose hard-earned physiological benefits of a fasted state. The ketone body component is also beneficial for users who train during the fasting period. While this is the period where fat burning is optimized, it can make training difficult because of relatively low levels of energy and motivation. The energy provided by the BHB ketone body component can help the user more effectively train with minimal disruption of the fasted state, while the paraxanthine component provides benefits of improved cognitive flexibility, improved sustained attention, improved working memory, enhanced inhibitory control, and minimization of undesirable side effects associated with hypoglycemia and downregulation of metabolic rate.

The ketone body component can also aid in inducing and sustaining a state of ketosis in the subject. For example, the ketone body component can help the body more quickly shift toward a fat-burning catabolic state. This can be particularly helpful during intermittent fasting, where the fat burning window at the end of the fasting period is relatively short. Similar results can be obtained when using 1,3-butanediol, which is readily converted to BHB in the body.

Moreover, even where a user is not necessarily in a fasted state, exogenous ketone body supplementation can benefit the user by aiding mitochondrial function while preserving blood glucose levels and glycogen stores, which then remain available for anabolic building of lean muscle as a result of exercise. This permits glucose, protein, and insulin to work together to build lean muscle mass when called upon rather than burned as energy sources. In addition, because excess ketone bodies, unlike sugars, are not converted into fat, they do not cause the simultaneous buildup of fat as when consuming a normal caloric intake of sugar, protein and fat.

Unexpectedly, it has now been found that the combination of BHB and paraxanthine in proper quantities and/or ratios provides for enhanced working memory, cognitive flexibility, inhibitory control and the ability to achieve sustained attention that would not have been predicted based on the individual effects of these components when used in isolation. For example, supplementation with a paraxanthine-BHB composition can lead to improvements in such desirable functional characteristics, without the secondary effects (e.g., jitters, racing hard, subsequent crash) typically associated with caffeine use, even where caffeine is metabolized into paraxanthine. Providing paraxanthine directly reduces or eliminates the concentration of theophylline and/or theobromine present within the blood stream of the user, which components are associated with such undesirable secondary effects.

In addition, the population at large does not metabolize caffeine at the same rates, and with the same results. For example, the enzyme cytochrome P450 1A2 is responsible for about 95% of all caffeine metabolism, and depending on genetics, some users produce more cytochrome P450 than other users. Because of this, the population at large includes fast metabolizers, intermediate metabolizers, and slow metabolizers of caffeine. Less than half the population is made up of fast metabolizers, where fast metabolizers generally achieve greater benefits with caffeine than intermediate or slow metabolizers. By providing paraxanthine directly, this provides a more uniform physiological and neurological response across a wide variety of users, regardless of whether such user is a fast metabolizer, an intermediate metabolizer, or a slow metabolizer of caffeine.

The paraxanthine-BHB compositions described herein may be provided in various forms, such as one-part or multi-part compositions configured for administration by one or more of ingestion, intragastric, injection, topical application, inhalation, oral mucosal administration, rectal administration, vaginal administration, or parenteral administration.

In an embodiment, the BHB comprises at least one of a BHB salt, a BHB ester, beta-hydroxybutyric acid, or a BHB precursor such as 1,3-butanediol.

In an embodiment, the composition may further include at least one fatty acid, or an ester of a fatty acid (e.g., a mono-, di-, or triglyceride), such as medium chain fatty acids, short chain fatty acids, and esters thereof. Medium chain fatty acids and esters thereof can be converted to BHB via lipolysis. The compositions may optionally include beta-hydroxy beta-methylbutyrate (HMB) in combination with BHB, as disclosed in U.S. Pub. No. 2022/0062216, which is incorporated herein by reference in its entirety.

In an embodiment, the composition may be provided in any of various forms, e.g., crystalline, powder, solid, liquid, solution, suspension, gel, etc.

In an embodiment, the composition is in a dosage form that provides from about 0.5 gram to about 50 grams, or about 1 gram to about 40 grams, or about 2 grams to about 30 grams, or about 3 grams to about 25 grams, or about 4 grams to about 20 grams, of the BHB (or precursor) per dose.

In an embodiment, the composition is in a dosage form that provides from about 25 mg to about 1000 mg, or about 50 mg to about 500 mg, or from about 75 mg to about 400 grams, or about 100 mg to about 300 mg, or about 125 mg to about 250 mg, of the paraxanthine per dose.

In an embodiment, the composition includes a pharmaceutically or dietetically acceptable carrier (e.g., water, ethanol, glycerin, propylene glycol, 1,3-propandiol, fruit juice, or food item).

Another exemplary embodiment may include paraxanthine, a plurality of anions comprising BHB anions, and a plurality of cations (e.g., alkali metal cations, alkaline earth metal cations, transition metal cations, and/or amino acid cations). Such an embodiment may be referred to as a "mixed salt".

An exemplary method may include administering paraxanthine, and administering a ketone body component or precursor that comprises at least one of beta-hydroxybutyrate (BHB) salts, BHB esters, BHB acid, or 1,3-butanediol.

An embodiment of such a method may include administering multiple doses per day. Exemplary dosage amounts of BHB and paraxanthine may be as noted above (e.g., about 0.5-50 grams, or about 1-40 grams, or about 2-30 grams, or about 3-25 grams, or about 4-20 grams of the BHB (or precursor); and about 25-1000 mg, or about 50-500 mg, or about 75-400 grams, or about 100-300 mg, or about 125-250 mg of the paraxanthine).

In an embodiment, the present compositions are substantially or entirely free of caffeine.

Such methods may provide for one or more of improved cognitive flexibility, improved sustained attention, improved working memory, enhanced inhibitory control, reduced lethargy or lightheadedness associated with hypoglycemia upon entering a ketogenic state, or maintenance or an increase in metabolic rate, even upon entering a ketogenic state. As will be shown within the accompanying expected data, the improvements in such areas are significantly better than what occurs when supplementing with caffeine, rather than paraxanthine. Other possible benefits may include homeostasis promotion, neuroprotection, memory enhancement, an anxiolytic effect, an anti-depressant effect, an anti-inflammatory effect, an analgesic effect, an antioxidant effect, blood pressure modulation, heart rate modulation, or a longevity promoting effect.

In an embodiment, the BHB increases the pharmacokinetic utilization of the paraxanthine relative to pharmacokinetic utilization of the paraxanthine in the absence of the BHB.

In an embodiment, the method can accelerate production of endogenous ketones in the user as a result of paraxanthine causing increased fat metabolism.

Additional features and advantages will be set forth in part in the description that follows, and in part will be obvious from the description, or may be learned by practice of the embodiments disclosed herein. It is to be understood that both the foregoing brief summary and the following detailed description are exemplary and explanatory only and are not restrictive of the embodiments disclosed herein or as claimed.

BRIEF DESCRIPTION OF DRAWINGS

Various objects, features, characteristics, and advantages of the invention will become apparent and more readily appreciated from the following description of the embodiments, taken in conjunction with the accompanying drawings and the appended claims, all of which form a part of this specification. In the Drawings, like reference numerals may be utilized to designate corresponding or similar parts in the various Figures, and the various elements depicted are not necessarily drawn to scale, wherein:

DETAILED DESCRIPTION

I. Introduction and Definitions

Figure 1:
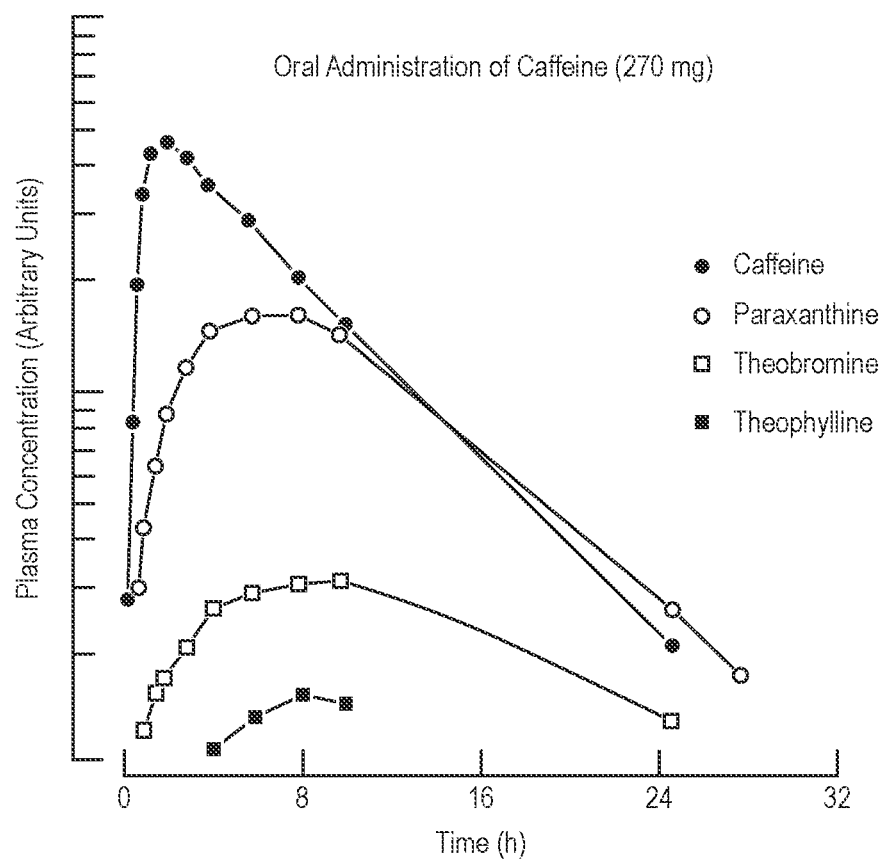
FIG. 1 shows relative blood plasma concentration levels of caffeine and its major metabolites associated with administration of caffeine.

Disclosed herein are compositions that include a combination of: (1) paraxanthine; (2) beta-hydroxybutyrate ("BHB"); and (3) optionally a dietetically or pharmaceutically acceptable carrier. Such combination compositions may be referred to herein as "Paraxanthine-BHB", or "BHB-Paraxanthine". Also disclosed herein are methods of using such compositions for neuroprotection, improved cognitive flexibility, improved working memory, reduced oxidative stress, minimizing or preventing lethargy or lightheadedness (e.g., low carb flu or keto flu) associated with entering a state of nutritional ketosis, minimizing or preventing downregulation of metabolic rate typically associated with entering a state of nutritional ketosis, or other benefits. In some embodiments, a BHB precursor such as 1,3-butanediol can be used in addition to or instead of BHB.

It has been found that combining paraxanthine with BHB results in a synergistic enhancement to one or more such functional characteristics within the user. For example, paraxanthine provides benefits of improved cognitive flexibility, the ability to achieve sustained attention, improved working memory, and enhanced inhibitory control. When paired with BHB, these benefits are synergistically enhanced, beyond any such benefit provided by either paraxanthine or BHB alone, and additional benefits are also provided, such as limiting effects of hypoglycemia upon entering a ketogenic state, maintaining or even increasing metabolic rate upon entering a ketogenic state, etc.

Such combinations also provide for improved results over a comparative combination of caffeine plus BHB, as the paraxanthine plus BHB does not exhibit the same undesirable secondary effects (subsequent crash, jitters, racing heartrate, increased incidence of mental errors, etc.) associated with caffeine. For example, by providing paraxanthine directly, rather than caffeine, in combination with BHB, the theophylline and theobromine that would metabolically result from use of caffeine are largely if not wholly eliminated, which components are believed to be at least partially responsible for the undesirable secondary effects associated with caffeine use (e.g., jitters, racing heart, increased mental errors, etc.). In addition, by providing BHB in such an environment (i.e., with paraxanthine, and in the general absence of theophylline and theobromine), the BHB, which is a ketone body capable of providing caloric energy, is able to more effectively be used, enhancing benefits such as improved cognitive flexibility, improved sustained attention, improved working memory, and enhanced inhibitory control. The combined use of paraxanthine and BHB also advantageously minimizes lethargy and lightheadedness associated with hypoglycemia upon entering a ketogenic state, as well as the typical downregulation of metabolic rate that occurs upon entering a ketogenic state.

A. Ketosis & Ketone Bodies

As discussed above, ketone bodies are produced from fat and are an alternative caloric source to glucose, particularly when glucose is not available, such as during periods of fasting, extreme exercise, and/or low carbohydrate consumption. When the body metabolically shifts to using ketone bodies as primary caloric energy, this is known as "ketosis". Ketone bodies can be used by cells of the body as a fuel in addition to or instead of glucose to satisfy the body's energy needs, including the brain and heart.

Upon transitioning into ketosis, during ketogenic metabolism in the liver, the body uses dietary and stored body fats as a primary energy source. The body initially cleaves fats into fatty acids and glycerol. It then transforms fatty acids into acetyl coenzyme A ("acetyl-CoA") molecules, which are then eventually transformed through ketogenesis into the water-soluble ketone bodies beta-hydroxybutyrate ("β-hydroxybutyrate" or "BHB"), acetoacetate, and acetone in the liver. BHB and acetoacetate are the ketone bodies used by the body for energy, while acetone is removed as a byproduct of ketogenesis. Although BHB is technically not a "ketone", it is still commonly referred to as a "ketone body" in the context of ketosis. The metabolism of ketone bodies is associated with several beneficial effects.

B. Intermittent Fasting

A method of fasting commonly referred to as "intermittent fasting" has increased in popularity in recent years as an alternative to long-term fasting. Intermittent fasting often involves entering into a state of ketosis. Because prolonged fasting is difficult and not fully sustainable over the long term, intermittent fasting attempts to provide many of the same benefits of fasting while minimizing the associated drawbacks. Although intermittent fasting, like prolonged fasting, involves entering into a catabolic state, intermittent fasting shortens the window of time within the day in which eating is allowed. For example, with a regular eater, there are about 16-18 hours between the time the first and last quantities of food are eaten. Intermittent fasting seeks to shorten this eating window. Intermittent fasting regimens vary, but all typically attempt to shorten the eating window to a time period of about 2-12 hours, more commonly about 4-10 hours, rather than the typical 16-18 hours.

Intermittent fasting provides similar benefits to prolonged fasting and nutritional ketosis. Although the fasting period in intermittent fasting typically does not last long enough for the user to completely deplete glycogen stores, ketosis typically begins to some degree after only about 12 hours of fasting. Intermittent fasting thus functions to train the body to utilize fat for energy, even if only for a few hours each day. In other words, as the body becomes more accustomed to longer periods of time between eating windows, it will become more metabolically flexible and able to more efficiently shift toward utilizing fats as a fuel source.

Intermittent fasting is also a popular regimen among athletes or those attempting to train specifically to achieve fat loss and achieve higher lean to fat mass ratios. Many schedule training sessions during the fasting period to more quickly deplete glycogen stores and thus accelerate or extend the fat burning window or to take advantage of beneficial hormone profiles during the fasting period. For example, many athletes may schedule training/workouts near the end of the fast when glycogen stores are more depleted and the body is metabolically shifted more towards a fat-burning state.

In some embodiments, a method of administering paraxanthine and beta-hydroxybutyrate (and/or precursor thereof) includes administering the composition while in a fasted state, such as during intermittent fasting. The composition will provide the person with increased energy, mental clarity, and other benefits that offset the lack of energy, mental clarity, and other negative effects of fasting. By combining fasting with the disclosed composition, a person can gain the benefits provided by fasting with the additional benefits provided by the composition. This may be referred to as "enhanced fasting" or "enhanced intermittent fasting".

C. Beta-Hydroxybutyrate and 1,3-Butanediol

The compound "beta-hydroxybutyrate," also known as β-hydroxybutyrate, 3-hydroxybutyrate, BHB, or BHB, is the deprotonated form of beta-hydroxybutyric acid, which is a hydroxycarboxylic acid having the general formula $CH_3CH_2OHCH_2COOH$. The deprotonated form present at typical biological pH levels is $CH_3CH_2OHCH_2COO^-$. The general chemical structure of Formula I below represents typical BHB compounds.

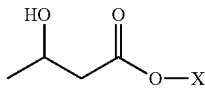

Formula I where X can be hydrogen, a metal ion, an amino cation such as from an amino acid, an alkyl group, an alkenyl group, an aryl group, or an acyl group.

When X is hydrogen, the compound is beta-hydroxybutyric acid. When X is a metal ion or an amino cation, the compound is a beta-hydroxybutyrate salt. When X is an alkyl group, an alkenyl group, an aryl group, or an acyl group, the compound is a beta-hydroxybutyrate ester.

1,3-Butanediol has the following chemical structure, is readily converted to beta-hydroxybutyrate in the body, and can therefore be used as a precursor for beta-hydroxybutyrate:

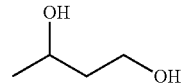

Like BHB, 1,3-butanediol has a chiral center and can be in the form of R-1,3-butanediol, S-1,3-butanediol, racemic mixture of R-1,3-butanediol and S-1,3-butanediol, or enriched in R-1,3-butanediol or S-1,3-butanediol. It is generally understood that chirality is maintained when 1,3-butanediol is converted to BHB such that R-1,3-butanediol is converted to R-beta-hydroxybutyrate in the body and S-1,3-butanediol is converted to S-beta-hydroxybutyrate.

Beta-hydroxybutyrate (BHB) is utilized by a patient's body as an energy source during instances of low glucose levels in the subject or when a patient's body is supplemented with a usable form of BHB. As noted above, although not technically a "ketone", one of skill in the art will recognize that BHB, in the context of ketosis, is commonly referred to as a "ketone body" because of its close relationship to and biological interplay with acetoacetate, which is a true ketone.

As noted, BHB may be provided in any of various forms, e.g., as beta-hydroxybutyric acid, as a beta-hydroxybutyrate salt, or as a beta-hydroxybutyrate ester. The foregoing compounds can be in any desired physical form, such as crystalline, powder, solid, liquid, solution, suspension, or gel.

Unless otherwise specified, the term "salt" does not mean or imply any particular physical state, such as a crystalline, powder, other solid form, dissolved in water to form a liquid solution, dispersed in a liquid to form a suspension, or gel. A salt can be formed in solution, such as by at least partially neutralizing beta-hydroxybutyric acid with a strong or weak base, such as an alkali or alkaline earth metal hydroxide, carbonate, or bicarbonate, basic amino acid, and the like.

BHB is a chiral compound and can exist as the R-enantiomer or the S-enantiomer, a racemic mixture, or a mixture where one of the enantiomers is enriched relative to the other. Endogenous BHB produced by the body is the R-enantiomer. BHB can be transformed by the body into acetoacetate, which is another ketone body utilized by the body, but which is not chiral, and acetoacetate can be transformed by the body back into the R-enantiomer of BHB. It is believed that the S-enantiomer of BHB can be transformed into the R-enantiomer by first being converted into acetoacetate and then into the R-enantiomer, or the body can utilize the acetoacetate directly. The S-enantiomer may also be highly bioactive in its own right, with unique pharmacokinetic and pharmacodynamic characteristics, although only a very small amount of the S-enantiomer is produced by the body, if at all.

In an embodiment, at least a portion of the BHB provided in the Paraxanthine-BHB product is provided as the S-enantiomer. Providing at least some of the S-enantiomer may provide benefits of increased alertness. For example, increased S-enantiomer of the BHB may allow for a more significant reduction in the paraxanthine dosage provided, while providing the same or similar benefits to increased alertness, improved working memory, improved cognitive flexibility, inhibitory control and sustained attention. By way of example, of the provided BHB, at least 1%, at least 3%, at least 5%, or at least 10% of the provided BHB may be of the S-enantiomer type. The S-enantiomer of the BHB may account for from 5% to 95%, from 5% to 75%, from 5% to 50%, from 10% to 50%, from 10% to 40%, or from 20% to 30% by weight of the provided BHB. The S-enantiomer of the BHB may account for 1%, 3%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% by weight of the BHB component. The S-enantiomer of the BHB component may be within a range having any two of the foregoing values as endpoints. The R-enantiomer of the BHB may provide principally caloric energy, while the S-enantiomer may enhance alertness and other mental clarity characteristics. The R-enantiomer may account for 1%, 3%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% by weight of the BHB component. The R-enantiomer of the BHB component may be within a range having any two of the foregoing values as endpoints.

D. Acetoacetate

Acetoacetate (AcAc) is another ketone body that can be included in the present formulations, in addition to BHB. AcAc is a true ketone and the deprotonated form of acetoacetic acid, which is a carboxylic acid having the formula $CH_3COCH_2COOH$. The deprotonated form present at typical biological pH levels is therefore $CH_3COCH_2COO^-$. As stated above, the body can transform BHB into acetoacetate and vice versa. As with BHB, acetoacetate may be utilized as an energy source during ketosis or when a patient's body is supplemented with a usable form of acetoacetate regardless of the body's state of energy utilization preference. The general chemical structure of Formula II represents acetoacetate compounds that may be utilized in the disclosed compositions (conformational isomers thereof may also be utilized):

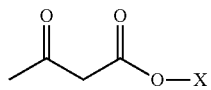

Formula II where X can be hydrogen, metal ion, amino cation, such as from an amino acid, alkyl, alkenyl, aryl, or acyl.

As with BHB, acetoacetate may be utilized by a patient's body as an energy source during instances of low glucose levels in the subject or when a patient's body is supplemented with a usable form of acetoacetate. Unlike BHB, acetoacetate is a true "ketone", and in the context of ketosis is commonly referred to as a "ketone body" along with BHB.

The beta-hydroxybutyrate and acetoacetate compounds described above may be collectively referred to herein as "ketone bodies," "exogenous ketone bodies," a "ketone body component," or "exogenous ketones."

Compositions as contemplated herein may also include ketone body precursors. Suitable ketone body precursors include, but are not limited to, beta-hydroxy beta-methyl-butyrate (HMB), 1,3-butanediol, medium chain fatty acids, and esters of medium chain fatty acids such as medium chain triglycerides. Ketone body compounds and ketone body precursor compounds are described in more detail below. While 1,3-butanediol is readily converted to BHB, HMB is metabolized in a complex cascade that may ultimately lead to formation of BHB but also may be converted into other substances or excreted in the urine.

E. Paraxanthine

Paraxanthine is a metabolite of caffeine, along with theophylline and theobromine. Upon ingestion, caffeine is metabolized primarily by demethylation to the above noted three dimethylxanthines. Metabolism of caffeine, as well as its dimethylxanthine metabolites is complex.

Shortly after ingestion, caffeine is metabolized into paraxanthine by hepatic cytochrome P450, which removes a methyl group from the N3 position of caffeine. After formation, paraxanthine can be broken down to 7-methylxanthine by demethylation of the NI position, which is subsequently demethylated into xanthine or oxidized by CYP2A6 into 1,7-dimethyluric acid. In another pathway, paraxanthine is broken down into 5-acetylamino-6-formylamino-3-methyluracil through N-acetyl-transferase 2, which is then broken down into 5-acetylamino-6-amino-3-methyluracil by non-enzymatic decomposition. In yet another pathway, paraxanthine is metabolized by CYP1A2 forming 1-methylxanthine, which can then be metabolized by xanthine oxidase to form 1-methyl-uric acid.

Like caffeine, paraxanthine is a psychoactive central nervous system (CNS) stimulant. Studies indicate that, similar to caffeine, simultaneous antagonism of adenosine receptors is responsible for paraxanthine's stimulatory effects. Paraxanthine adenosine receptor binding affinity appears to be similar or slightly stronger than caffeine, but weaker than theophylline.

Paraxanthine is a selective inhibitor of cGMP-preferring phosphodiesterase (PDE9) activity and is thought to increase glutamate and dopamine release by potentiating nitric oxide signaling. Activation of a nitric oxide-cGMP pathway may be responsible for some of the behavior effects of paraxanthine that differ from those associated with caffeine.

Paraxanthine is also a competitive nonselective phosphodiesterase inhibitor which raises intracellular cAMP, activates PKA, inhibits TNF-alpha and leukotriene synthesis, and reduces inflammation and innate immunity.

Unlike caffeine, paraxanthine acts as an enzymatic effector of Na+/K+ATPase. As a result, it is responsible for increased transport of potassium ions into skeletal muscle tissue. Similarly, the compound also stimulates increases in calcium ion concentration in muscle.

The pharmacokinetic parameters for paraxanthine are similar to those of caffeine, but differ significantly from those for theobromine and theophylline, the other major caffeine-derived methylxanthine metabolites in humans.

While paraxanthine supplementation has been studied for a variety of biological effects, and while positive results have often been noted, paraxanthine is an expensive component to source, and the effects typically appear to be relatively minor or somewhat inconsistent. Thus, although paraxanthine supplementation appears to have great potential for achieving various health and/or performance benefits, there is an ongoing need for determining bio-mechanisms, compositions and methods capable of utilizing and/or enhancing the effects of paraxanthine to levels that can significantly benefit health and performance.

F. Stacked Ketone Bodies & Mixed Cation Salts

Any of the compositions described herein may include other ketone bodies, in combination with the BHB. Such compositions may comprise a "stacked composition". The terms "stacked composition," "keto-stack," "stack," "ketone body stack," and variations thereof are used herein to refer to a composition including at least two separate compounds selected from: (i) a beta-hydroxybutyrate salt; (ii) an acetoacetate salt; (iii) a beta-hydroxybutyrate ester; (iv) an acetoacetate ester; (v) beta-hydroxybutyrate free acid (i.e., beta-hydroxybutyric acid); and (vi) acetoacetate free acid (i.e., acetoacetic acid), where at least one of the stack is a BHB compound.

A stacked composition may include a combination of compounds selected from (i) through (vi) such that there are at least two of (A)-(C), where: (A) represents one or more salts; (B) represents one or more esters; and (C) represents one or more free acids. At least one of the salts, esters, or free acids is a BHB compound.

Exemplary salt forms include sodium, potassium, calcium, magnesium, and lithium. Some embodiments include one or more transition metal salts. Transition metal cations suitable for use as part of a salt include chromium, manganese, cobalt, copper, zinc, iron, (e.g., as an iron II or iron III cation), molybdenum, and selenium. Other suitable salt forms include cations of organic compounds capable of having a net positive charge, including amino acids or their derivatives/metabolites such as arginine, lysine, leucine, iso-leucine, histidine, ornithine, creatine, agmatine, L-glutamine, and citrulline.

Suitable ester forms include mono-esters of ethanol, mono-esters of 1-propanol, mono-esters of 1,3-propanediol, di-esters of 1,3-propanediol, mono-esters of S-1,3-butanediol, mono-esters of R-1,3-butanediol, di-esters of 1,3-butanediol, mono-esters of glycerin, di-esters of glycerin, and tri-esters of glycerin. 1,3-butanediol is a metabolic BHB precursor that may additionally be utilized for in vivo generation of BHB and/or acetoacetate compounds. The acid forms typically have an unpleasant taste but can be used by appropriate taste masking mechanisms, such as one or more capsules, tablets, or other bolus.

Each of the different forms (salt, acid, ester) has its own properties and its own potential benefits and limitations. For example, ester forms of beta-hydroxybutyrate typically have poor organoleptic properties relative to the other forms of beta-hydroxybutyrate. That is, ester forms of beta-hydroxybutyrate are often described as having a pungent taste and/or smell.

Salt forms are generally considered to taste better than ester forms. However, administration of clinically or dietetically effective doses of components in salt form inherently requires administration of relatively high levels of the corresponding cations. Sodium, for example, is often used as the cation in beta-hydroxybutyrate salts, and high levels of sodium have well-known negative health effects (e.g., elevated blood pressure). By way of further example, calcium is often used as the cation in HMB salts, and high levels of calcium can also be detrimental to health, particularly when not balanced by other cations. Although different salts having different cations may be mixed to dilute the impact of a single cation, it can still be difficult to provide effective amounts of BHB or other ketone bodies without upsetting the electrolyte balance in the subject, when relying on use of salts alone.

The free acid forms of beta-hydroxybutyrate (i.e., beta-hydroxybutyric acid) and acetoacetate (i.e., acetoacetic acid) can be used. However, because of the relatively low pKa values (e.g., beta-hydroxybutyric acid has a pKa of 4.70), these compounds deprotonate and produce $H^+$ at physiological pH. The resulting excess acidity can cause undesirable side effects including causing or aggravating gastrointestinal issues such as ulcers or reflux.

1,3-Butanediol can be used in a keto-stack, is neither acidic or a salt, and is readily converted to beta-hydroxybutyrate in the body. However, the amount of 1,3-butanediol that can be administered is limited by its ability to provide intoxicating effects, similar to ethanol. Thus, 1,3-butanediol may be advantageously used in addition to beta-hydroxybutyrate to provide an additional quantity of beta-hydroxybutyrate without providing additional electrolytes or acidity. In some cases, it may be desirable to administer 1,3-butanediol in a sub-intoxicating dose, which depends on the weight, sex and other aspects of the user, such as less than 30 grams, 25 grams, or 20 grams. Nonetheless, administering an intoxicating dose (e.g., at least 30 grams, 40 grams, or 50 grams) can be desirable in some cases, such as where the user is at a party and wishes to obtain the benefits of the disclosed composition together with a feeling of increased relaxation and confidence.

Providing different amounts or ratios of R-beta-hydroxybutyrate and S-beta-hydroxybutyrate can be a form of stacking, since they are different ketone bodies that provide different physiological effects. It may be desirable to provide BHB as pure R-beta-hydroxybutyrate or enriched relative to S-beta-hydroxybutyrate to increase potency. Alternatively, it may be desirable to provide BHB as pure S-beta-hydroxybutyrate or enriched relative to R-beta-hydroxybutyrate to decrease potency and increase long-term effects. Administering R-beta-hydroxybutyrate, the endogenous form, results in attaining rapid elevated ketosis, while administering S-beta-hydroxybutyrate, which must first be converted to acetoacetate, and then optionally to R-beta-hydroxybutyrate, may provide slower and more sustained ketosis. As noted above, S—BHB also provides benefits of increased alertness in addition to its potential as a caloric energy source, as compared to R—BHB, which provides principally caloric energy benefits.

Combining or stacking different salt types and/or different forms of BHB and acetoacetate can beneficially limit the occurrence or severity of these undesirable side-effects and/or can permit administration of higher doses of such components. For example, a mixed salt composition comprising different cations or a stacked form can deliver the same amount of ketones bodies as a single form without causing the same occurrence and/or severity of side-effects. Likewise, a mixed salt form or stacked form can deliver a greater amount of BHB or acetoacetate as compared to a single form before reaching similar occurrence and/or severity of side-effects.

In other words, for a given dose of BHB or acetoacetate, a stacked form is expected to have less 1) undesirable organoleptic side-effects, 2) electrolyte imbalance side-effects, and/or 3) acidity side-effects as compared to the single form. For example, a single form ester may have a threshold dosage that the typical user will not exceed because of the negative organoleptic side-effects, a single form salt may have a threshold dosage limited by the recommended dietary limits of the electrolytes administered with the salt, and a single form acid may have a threshold dosage that the typical user will not exceed because of the negative effects of acidity. The combined or stacked forms may allow supplementation of greater amounts of BHB and/or acetoacetate without exceeding any of the thresholds related to organoleptic, electrolyte, or acidity side-effects.

In some embodiments, the composition includes at least about 2% of ester forms, at least about 2% of salt forms, and/or at least about 2% of free acid forms on a molar basis. In other words, at least about 2% of the number of molecules (BHB and/or acetoacetate) can be provided by each separate form, or at least two forms. More preferably, a composition includes at least about 5% ester form, at least about 5% salt form, and/or at least about 5% free acid form on a molar basis, or at least about 10% ester form, at least about 10% salt form, and at least about 10% free acid form on a molar basis, or at least about 20% ester form, at least about 20% salt form, and at least about 20% free acid form on a molar basis, or at least about 30% ester form, at least about 30% salt form, or at least about 30% free acid form on a molar basis.

In some embodiments, the composition includes an ester form at about 2% to about 96%, or about 5% to about 90%, or about 10% to about 80%, or about 20% to about 60% on a molar basis, includes a salt form at about 2% to about 96%, or about 5% to about 90%, or about 10% to about 80%, or about 20% to about 60% on a molar basis, and includes an acid form at about 2% to about 96%, or about 5% to about 90%, or about 10% to about 80%, or about 20% to about 60% on a molar basis.

G. Other Definitions

As used herein, "subject," "patient," or "user" refers to mammals, including humans and other primates. The subject may be any mammal requiring metabolic therapy, treatment, or prophylaxis, or any mammal suspected of requiring metabolic therapy, treatment, or prophylaxis. Prophylaxis means that a regimen is undertaken to prevent a possible occurrence, such as where a high risk of diabetes or other metabolic disorder is identified. "Patient," "subject," and "user" are used interchangeably herein.

"Ketosis" as used herein refers to the metabolic state entered during an intermittent fasting period or a longer fasting period (e.g., 2 days or more). A subject can also be considered to be in ketosis when the subject has blood ketone levels within the range of about 0.5 mmol/L to about 16 mmol/L. Ketosis may improve mitochondrial function, decrease reactive oxygen species production, reduce inflammation and increase the activity of neurotrophic factors. "Keto-adaptation" as used herein refers to prolonged nutritional ketosis (>1 week) to achieve a sustained nonpathological "mild ketosis" or "therapeutic ketosis," or it denotes an altered metabolism in which fat becomes the predominant energy source, consequently shifting the body from a state of fat storage to a state of fat oxidation. It is believed that administering BHB and other ketone bodies in doses disclosed herein can provide the same or similar benefits as being in a state of ketosis even if the subject has not achieved a sufficiently high blood ketone level to technically be in a state of ketosis.

The term "administration" or "administering" is used herein to describe the process in which the disclosed compositions are delivered to a subject. "Administration" and "administering" can include any known method or configuration that can deliver the disclosed compositions to blood, tissues and/or cells, whether to a targeted region, widely diffused, or systemic.

The term "unit dose" refers to a dosage form that is configured to deliver a specified quantity or dose of composition or component thereof. Example dosage forms include, but are not limited to, tablets, capsules, powders, food products, food additives, beverages (such as flavored, vitamin fortified, or non-alcoholic), beverage additives (such as flavored, vitamin fortified, or non-alcoholic), candies, suckers, pastilles, food supplements, dietetically acceptable sprays (such as flavored mouth spray), injectables (such as an alcohol-free injectable), and suppositories. Such dosage forms may be configured to provide a full unit dose or fraction thereof (e.g., ½, ⅓, or ¼ of a unit dose).

Another dosage form that can be used to provide a unit dose of composition or component thereof is a unit dose measuring device, such as a cup, scoop, spatula, syringe, dropper, spoon, or suppository injection device, which is configured to hold therein a measured quantity of composition equaling a full unit dose or fraction thereof (e.g., ½, ⅓, or ¼ of a unit dose). For example, a bulk container, such as a carton, box, can, jar, bag, pouch, bottle, jug, or keg, containing several unit doses of composition (e.g., 5-250 or 10-150 unit doses) can be provided to a user together with a unit dose measuring device that is configured to provide a unit dose, or fraction thereof, of composition or component thereof.

A kit for use in providing a composition as disclosed herein in bulk form, while providing unit doses of the composition, may comprise a bulk container holding therein a quantity of composition and a unit dose measuring device configured to provide a unit dose, or fraction thereof, of composition or component thereof. One or more unit dose measuring devices may be positioned inside the bulk container at the time of sale, attached to the outside of the bulk container, prepackaged with the bulk container within a larger package, or provided by the seller or manufacturer for use with one or multiple bulk containers.

The kit may include instructions regarding the size of the unit dose, or fraction thereof, and the manner and frequency of administration. The instructions may be provided on the bulk container, prepackaged with the bulk container, placed on packaging material sold with the bulk container, or otherwise provided by the seller or manufacturer (e.g., on websites, mailers, flyers, product literature, etc.) The instructions for use may include a reference on how to use the unit dose measuring device to properly deliver a unit dose or fraction thereof. The instructions may additionally or alternatively include a reference to common unit dose measuring devices, such as spoons, spatulas, cups, and the like, not provided with the bulk container (e.g., in case the provided unit dose measuring device is lost or misplaced). In such case, a kit may be constructed by the end user when following instructions provided on or with the bulk container, or otherwise provided by the seller regarding the product and how to properly deliver a unit dose of composition, or fraction thereof.

II. Paraxanthine-BHB Compositions

Paraxanthine-BHB compositions described herein may comprise: (1) paraxanthine; (2) a ketone body (KB) component including beta-hydroxybutyrate (BHB); and (3) optionally a dietetically or pharmaceutically acceptable carrier. Additional ketone body components such as acetoacetate (AcAc) may also be included with the KB of (2). In some embodiments, a BHB precursor such as 1,3-butanediol can be used in addition to or instead of BHB. Similarly, although HMB is technically not a ketone body, it may also be included in the composition, providing benefits associated with a combination of BHB and HMB, as described in U.S. Pub. No. 2022/0062216, which is incorporated by reference.

As described above, paraxanthine-BHB compositions may be formulated with various ratios of paraxanthine to BHB. While ratios may vary, as BHB serves as a caloric energy source, and the paraxanthine is provided not for caloric energy, but for its pharmacokinetic and pharmacodynamic benefits, the dosage of BHB may typically be greater than that of paraxanthine. For example, the BHB to paraxanthine ratio may be at least 1:1, 1.25:1, 1.5:1, 2:1, 4:1, 5:1, 6:1, 9:1, or may be within a range having any two of the foregoing ratios as endpoints. The ratio may be formulated according to particular application needs and preferences. While providing BHB alone may provide for enhanced metabolic activity (e.g., fat loss, anti-inflammation, vasodilation), when provided in combination with paraxanthine, synergistic results are believed to be provided, e.g., including enhancements to such metabolic benefits, but also neuroprotection, enhanced focus and clarity, cognitive flexibility, improved working memory, improved response times, reduced oxidative stress, modulation of lethargy/lightheadedness typically associated with hypoglycemia upon entering a ketogenic state, moderation of the typical downregulation of metabolic rate upon entering a ketogenic state, etc.

Various additional additives that may be present in an energy formulation include any of those described in U.S. Pub. No. 2021/026724, which is incorporated by reference.

A paraxanthine-BHB composition may also optionally include a supplemental source of ketone body precursors such as one or more of 1,3-butanediol, fatty acids, and/or esters of fatty acids. A typical ester form of fatty acids is a mono-, di-, or triglyceride. Preferred forms of fatty acids and their esters are medium chain fatty acids and medium chain triglycerides (MCT), though short and/or long chain fatty acids and their esters may also be utilized. In embodiments where used, a medium chain fatty acid has from 6 to 12 carbons, preferably from 8 to 10 carbons. Compositions and methods related to the combination of BHB with a medium chain fatty acid, or ester thereof, are disclosed in U.S. Pat. No. 9,138,420, which is incorporated by reference.

Exemplary medium chain fatty acids are caproic acid, also known as hexanoic acid having 6 carbons, caprylic acid, also known as octanoic acid having 8 carbons, capric acid, also known as decanoic acid having 10 carbons, and lauric acid, also known as dodecanoic acid having 12 carbons. Because MCTs are ketone body precursors, including one or more MCTs may provide an additional source for the production of ketone bodies independent of the BHB and any acetoacetate compounds, thus helping to promote sustained elevation of ketone levels to a desired therapeutic level.

The term "short chain triglycerides" (SCT) refers to molecules similar to MCT molecules but with short chain fatty acids (less than 6 carbon atoms in length) attached to the glycerol backbone. The term "long chain triglycerides" (LCT) refers to molecules similar to MCT molecules but with long chain fatty acids (more than 12 carbon atoms in length) attached to the glycerol backbone.

Examples and sources of the medium chain fatty acid, or an ester thereof such as a medium chain triglyceride, include coconut oil, coconut milk powder, fractionated coconut oil, palm oil, palm kernel oil, caprylic acid, isolated medium chain fatty acids, such as isolated hexanoic acid, isolated octanoic acid, isolated decanoic acid, medium chain triglycerides either purified or in natural form such as coconut oil, and ester derivatives of the medium chain fatty acids ethoxylated triglyceride, enone triglyceride derivatives, aldehyde triglyceride derivatives, monoglyceride derivatives, diglyceride derivatives, and triglyceride derivatives, and salts of the medium chain triglycerides. Ester derivatives optionally include alkyl ester derivatives, such as methyl, ethyl, propyl, butyl, hexyl, etc. derivatives.

When medium chain fatty acids, fatty acid esters, or mono-, di- or triglycerides of medium chain fatty acids are provided, the composition is preferably administered such that the weight ratio of ketone bodies (e.g., BHB) to medium chain fatty acid (or ester thereof) ranges from about 4:1 to about 1:4, or from about 2:1 to about 1:2, or from about 1.5:1 to about 1:1.5. The same ratios may be used when short chain fatty acids (or esters thereof) or long chain fatty acids (or esters thereof) are additionally or alternatively used.

Examples of short chain fatty acids include acetic acid, propionic acid, butyric acid, isobutyric acid, valeric acid, and isovaleric acid. Examples of medium chain fatty acids include caproic acid, caprylic acid, capric acid, and lauric acid. Examples of long-chain fatty acids include myristic acid, palmitic acid, stearic acid, arachidic acid, behenic acid, lignoceric acid, cerotic acid, omega-3 fatty acids, omega-6 fatty acids, omega-7 fatty acids, and omega-9 fatty acids.

III. Treatment Effects

The administration of a paraxanthine-BHB composition may provide a variety of beneficial physiological and neurological effects, including one or more of neuroprotection, enhanced focus and clarity, cognitive flexibility, improved working memory, improved response times, potentiation of vasodilator (e.g., nitric oxide) neurotransmitter signaling, modulation of lethargy/lightheadedness typically associated with hypoglycemia upon entering a ketogenic state, and moderation of the typical downregulation of metabolic rate upon entering a ketogenic state. Additional benefits may include reduced oxidative stress, antioxidant effects, analgesic effects, anti-inflammatory effects, as well as fat loss, appetite suppression and enhanced inhibitory control, anxiety mediation, suppression of depressive symptoms, cardiovascular benefits (e.g., vasodilation and blood pressure modulation), and anti-aging/longevity, for example.

Though a variety of different pharmacological and/or physiological variables may be involved, the combination compositions described herein may enable complementary enhancement of several different neurological and physiological systems. Without being bound to any particular theory, it is presently believed that the paraxanthine component functions to provide enhancements similar to that provided by caffeine, but while eliminating undesirable side effects associated with caffeine, and reducing or eliminating differences in how such a psychostimulant is metabolized by different users. In addition, paraxanthine provides benefits not provided by caffeine, such as potentiation of vasodilator neurotransmitter signaling. While some such benefits are known to occur with paraxanthine supplementation alone, by providing the paraxanthine with BHB, the provided benefits are enhanced, beyond what would be predicted or expected, based on additive effects alone. In other words, synergistic benefits result, from the combination of both paraxanthine and BHB, which benefits are not provided with either component independently.

The beneficial treatment effects described herein may be achieved or enhanced when the subject is in a state of ketosis, or entering a ketogenic state, due to the BHB component of the composition. Although many of the examples may be described in the context of a subject entering or being in a state of ketosis, such as while fasting, it will be understood that realization of the beneficial effects does not necessarily require the subject to be in such a state. For example, numerous neurological benefits, such as enhanced focus and clarity, improved cognitive flexibility, improved working memory, improved response times, potentiation of vasodilator neurotransmitter signaling, and neuroprotection may be provided, even where the subject may not necessarily be in a state of ketosis. When in a state of ketosis, such benefits may be provided, as well as modulation of lethargy/lightheadedness typically associated with entering a ketogenic state, modulation of the down-regulation of metabolic rate that is typical of a ketogenic state, fat loss, muscle maintenance, etc. In other words, beneficial effects may be realized as a result of co-administration of the exogenous ketone body component BHB and paraxanthine. These effects may be further enhanced once the subject enters an active state of ketosis, and the BHB component can itself aid in getting the subject into such a state, but ketosis is not necessarily a requirement for realizing the benefits described herein.

A. Metabolism of Caffeine vs. Paraxanthin

Figure 2:
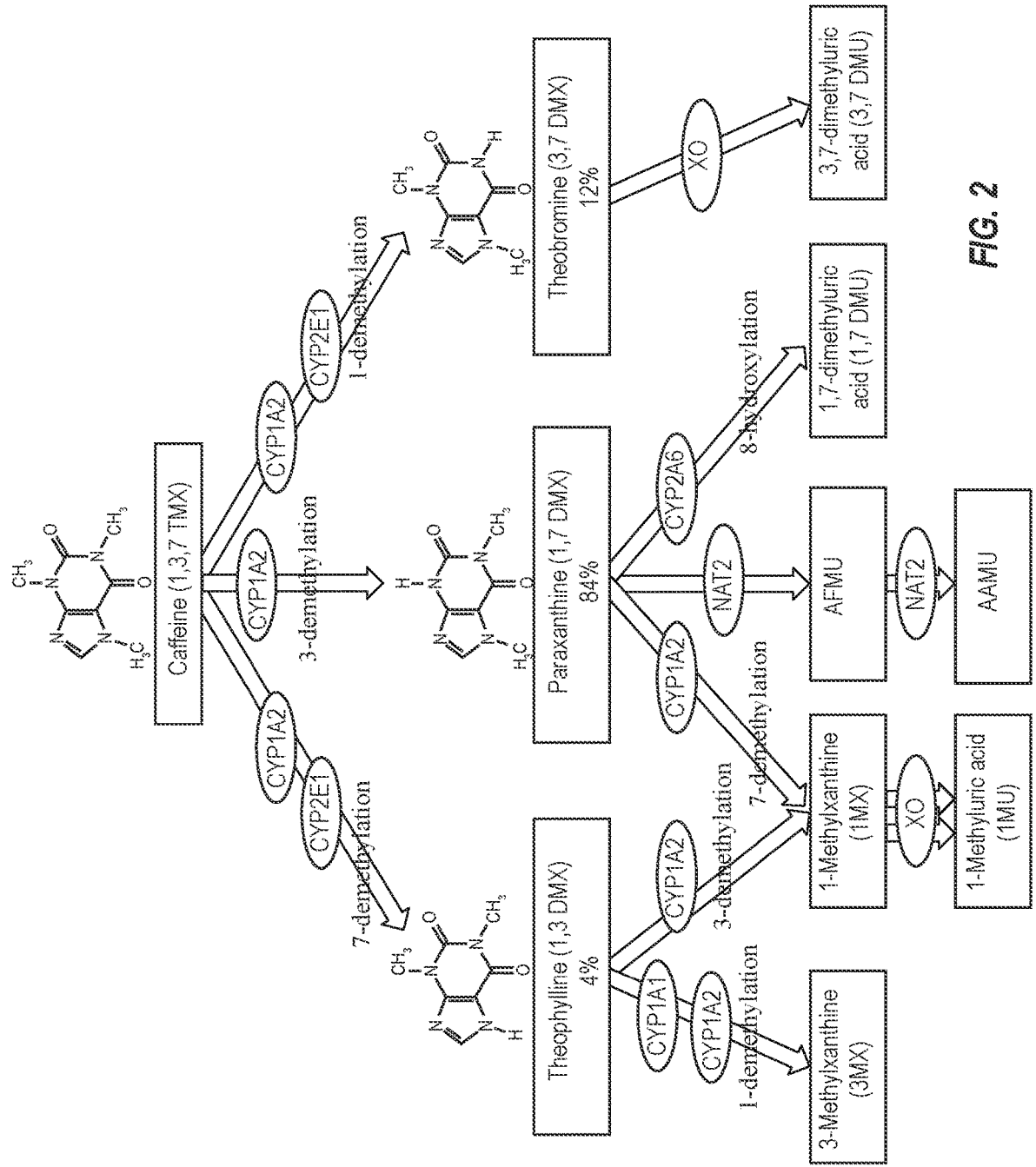
FIG. 2 illustrates a simplified exemplary metabolic pathway for metabolism of caffeine.

FIG. 1 illustrates exemplary blood plasma concentration curves for caffeine and its metabolites (paraxanthine, theophylline, and theobromine), upon oral administration of 270 mg of caffeine. Paraxanthine (1,7-dimethylxanthine) accounts for about 70-72% of caffeine ingested, and about 84% of the methylxanthine metabolic by-products. As shown in FIG. 2, theophylline and theobromine account for 4%, and 12% respectively, of the methylxanthine metabolic by-products.

Figure 3:
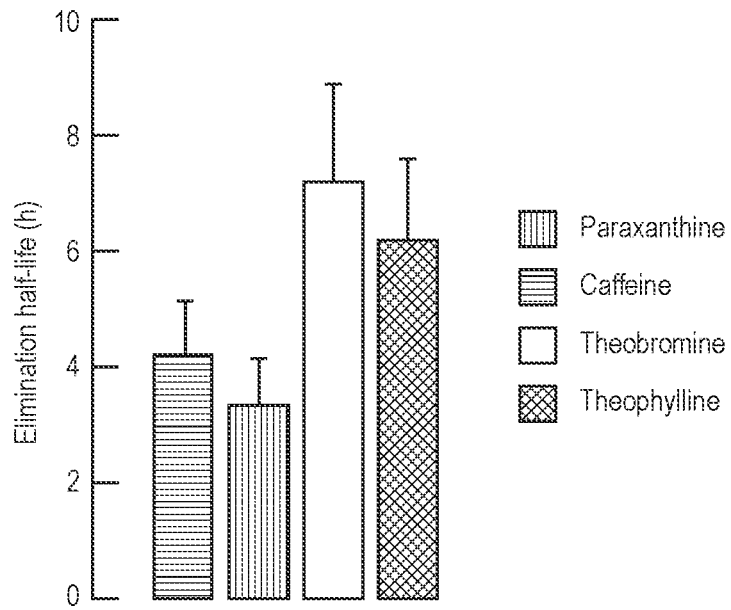
FIG. 3 illustrates the elimination half-life of paraxanthine as compared to that of caffeine, theophylline, and theobromine.

Paraxanthine is a natural dietary component that can be found in small amounts in *Theobroma cacao* fruits, *Coffea arabica, Sinomenium actum*, as well as the stamens of citrus flowers, for example. As shown in FIG. 3, paraxanthine has a shorter half-life, and faster clearance than caffeine, or theophylline or theobromine. For example, the half-life of paraxanthine is 3.1 hours, significantly shorter than that of caffeine (4.1 hours), and half or less than that of theophylline (6.2 hours) and theobromine (7.2 hours). Total plasma clearance of paraxanthine (2.20 mL/min/kg) is greater than that of caffeine (2.07 mL/min/kg), and far greater than that of theophylline (0.93 mL/min/kg) or theobromine (1.2 mL/min/kg).

Paraxanthine provides significant benefits (and minimizes negative side effects) as compared to use of caffeine. For example, paraxanthine is less toxic than caffeine, is less clastogenic as compared to caffeine or theophylline, and is less teratogenic as compared to caffeine or theophylline. Like caffeine, paraxanthine is a psycho and central nervous system stimulant. Paraxanthine is believed to work through a mechanism of being an adenosine receptor antagonist. Paraxanthine provides stronger locomotor activation effects than caffeine, with higher binding potencies for adenosine A1 and A2a receptors. Blocking of A1 receptors increases neurotransmitter release (e.g., glutamate and dopamine). Advantageously, in addition to being an adenosine receptor antagonist, paraxanthine also potentiates nitric oxide (a vasodilator) neurotransmitter signaling. Caffeine provides no such benefit. It is believed that phosphodiesterase 9 (PDE9) terminates nitric oxide neurotransmission by metabolizing cGMP back to GMP. Paraxanthine inhibits PDE9, thereby potentiating nitric oxide neurotransmission and dopamine release. As noted, caffeine does not have this effect.

Paraxanthine is a stronger, more potent neuroprotective than caffeine. For example, paraxanthine has been shown to protect dopaminergic neurons, and is strongly protective against neurodegeneration and the loss of synaptic function, whereas caffeine only provides marginal protection for such.

Interestingly, paraxanthine has stronger wake promoting activity as compared to caffeine, while also being longer lasting than caffeine. Such is interesting given that paraxanthine has a shorter half-life, and faster clearance (paradoxically, paraxanthine has a shorter half-life, and shorter clearance, but is both more potent and longer lasting). As noted, paraxanthine is less toxic than caffeine. For example, elevated doses of caffeine (as well as modafinil) induce hypothermia and reduced locomotor activity. At similar doses, no such problems are observed with paraxanthine.

As noted previously, importantly, different persons metabolize caffeine differently, depending on their genetic characteristics. For example, the enzyme cytochrome P450 1A2 is responsible for about 95% of all caffeine metabolism, including the demethylation of caffeine to paraxanthine. Subjects who have a homogenous A allele of the CYP1A2 gene tend to produce more cytochrome P450, and consequently metabolize caffeine more quickly. Fast metabolizers of caffeine more consistently experience greater ergogenic outcomes in some (but not all) studies. The problem is that less than 50% of the population are fast metabolizers, meaning that the majority of subjects miss out on such benefits that those who are fast metabolizers achieve with caffeine. By using paraxanthine directly, this avoids the effect associated with genetic differences in subjects, allowing those who are intermediate or slow metabolizers of caffeine to benefit more optimally.

The use of paraxanthine, rather than caffeine provides numerous benefits, some of which are noted above. An additional organoleptic benefit is provided in that paraxanthine is less bitter than caffeine, making it easier to formulate with. When paired with BHB, even less paraxanthine is required to achieve a given benefit, making it even easier to formulate with. Table 1 below shows results of a taste test, evaluating bitterness, as tested using a specially trained taste panel. Each solution was prepared by dissolving 163 mg of the component to be tested for bitterness, into 473 mL of water. As a comparative reference point, caffeine provides a bitterness score of 5.0. Solution L was for Liberine, Solution T was for Theacrine, Solution M was for methylliberine, and Solution P was for paraxanthine. With an average bitterness score of 3.9, paraxanthine provides a significantly less bitter taste than caffeine (5.0), and is far less bitter than the other tested components.

TABLE 1

Bitterness Score

|  | Solution L (163 mg/ 473 mL) | Solution P (163 mg/ 473 mL) | Solution T (163 mg/ 473 mL) | Solution M (163 mg/ 473 mL) |
| --- | --- | --- | --- | --- |
| Tester 1 | 11.4 | 4.2 | 12.6 | 14.7 |
| Tester 2 | 10.7 | 3.7 | 11.3 | 13.8 |
| Tester 3 | 10.5 | 4.4 | 11.8 | 13.4 |
| Tester 4 | 10.9 | 3.7 | 12.7 | 14.3 |
| Tester 5 | 10.5 | 3.9 | 11.9 | 14.0 |
| Tester 6 | 11.4 | 3.7 | 13.0 | 14.5 |
| Tester 7 | 10.8 | 3.6 | 12.5 | 14.6 |
| Tester 8 | 11.2 | 4.0 | 13.0 | 14.3 |
| Tester 9 | 10.9 | 3.9 | 11.9 | 14.2 |
| Tester 10 | 11.1 | 4.2 | 12.4 | 14.2 |
| Average | 10.9 | 3.9 | 12.3 | 14.2 |

While the above-described effects of paraxanthine are independently desirable, it has been surprisingly found that the combination of paraxanthine and BHB surprisingly enhances the benefits provided by paraxanthine, and reduces the amount of paraxanthine needed to provide a given benefit level. For example, because the BHB component both provides caloric energy, without an insulin spike, and also promotes more efficient use of fat for energy purposes, there is greater energy available to the subject via available ketone bodies, to perform work, enhancing the cognitive flexibility, enhanced ability to sustain attention, maintain clarity, and benefit from the enhanced working memory associated with paraxanthine supplementation. The caloric energy provided by the BHB in combination with the paraxanthine also modulates the lethargy/lightheadedness typically associated with entering a ketogenic state, while also modulating the typical downregulation of metabolic rate associated with entering a ketogenic state. As shown in the accompanying expected data, metabolic rate can be maintained, or even increased when a user supplements with such a combination. As will be shown in the accompanying data, these benefits, and the performance of a given subject supplementing with paraxanthine in combination with BHB is significantly enhanced, as compared to a similar subject who is only supplementing with paraxanthine alone, or supplementing with BHB alone, or only supplementing with caffeine alone, or a combination of caffeine and BHB.

The following figures illustrate such expected improvements, through various clinical studies. For example, one clinical study compares results of supplementation with paraxanthine in combination with BHB, as compared to supplementation with paraxanthine alone, as compared to supplementation with BHB alone, as compared to supplementation with a placebo. The subjects include healthy young adults, of mixed gender, with administration of four executive function tests that evaluate working memory, inhibitory control, cognitive flexibility, and sustained attention. Working memory is the ability to hold information in the mind, and work with it. The ability to remember instructions, create a plan of action, and pay attention are all dependent upon a working memory. Inhibitory control is the ability to control attention, behavior, thoughts, and emotions, instead of acting on impulse or desire. Cognitive flexibility is the ability to change tasks, adjust to changed demands, changed priorities, and changed perspectives. Sustained attention is the ability to focus on an activity or stimulus over a long period of time (e.g., 2-3 hours or more). It is what makes it possible to concentrate on an activity for as long as it takes to finish, even if there are other distracting stimuli present.

Attention and inhibitory control can be measured using a Go/No Go Test, which is used to measure a participant's capacity for sustained attention and response control. The Go/No Go Test is routinely used in the field, and will be familiar to those of skill in the art. In the Go/No Go Test, participants watch a 2×2 array of squares, and then there is a successive presentation of letters (e.g., either P or R) and the participant responds to a target letter by pressing the corresponding button on a keyboard. The single letter (P or R) is presented in one of the 4 squares for 500 milliseconds, with 1500 milliseconds between subsequent stimuli. For the P-Go condition, participants are asked to press the P key in response to the letter P, and abstain from responding to the letter R. For the R-reversal condition, the participants are asked to respond to the letter R, and abstain when seeing the letter P. Mean response time, as well as percentage of correct answers are recorded.

The Vigilance Task Test is another test routinely used in the field, and is used to evaluate a participants ability to sustain attention. The Vigilance Task Test is a sustained attention, reaction timed task test that measures the speed with which participants respond to a visual stimulus. The subjects respond to visual stimuli (e.g., a red dot) by pressing a key as soon as it appears on the computer screen. The light turns on at random, e.g., roughly every couple of seconds or so during the test. The speed of response is measured. Due to the random nature of the test, there is no learning effect. Mean response time is recorded.

The Berg-Washington Card Sorting Task (BCST) test is a test routinely used in the field to evaluate cognitive flexibility. The BCST test focuses on basic cognitive flexibility or set-shifting between old vs. new rule changes. The test involves reasoning, learning, executive control, and attention shifting. It is particularly sensitive to the subject's inability to shift set. Cards are shown with different colors (e.g., red, green, yellow, blue), different designs (e.g., circle, triangle, star, plus sign) and different numbers of symbols (e.g., 1-4) on the computer screen. Participants are asked to sort the cards by matching colors and/or designs and/or number of symbols, where the instruction for how to sort the cards can change, at different times during the test. Number of correct responses and number of errors (particular perservative errors, where the participant incorrectly continues sorting the cards under an old instruction, after a new instruction is given) are recorded.

The Sternberg Test is a test routinely used in the field to evaluate working memory, and ability to make use of short-term memory. A lower reaction time means that participants can access their working memory faster. The Sternberg Task Test is a widely used paradigm for studying short term/working memory involving cognitive control processes. Participants are asked to remember a short series of letters or other characters and then the participants has to respond if the series of letters or characters is present in a larger series of letters or characters. Reaction time is measured when the remembered short series is both present or absent. Mean response time is recorded.

When running each such tests, subjects are given either paraxanthine+BHB, paraxanthine alone, BHB alone, or a placebo. The dosage amounts are 200 mg paraxanthine and 5 g of BHB, 200 mg of paraxanthine alone, 5 g of BHB alone, or a placebo. The testing is conducted under double blind, placebo controlled conditions. The subjects include 13 healthy young adults (10 male, 3 female), aged 24±5 years; height 170.0±11.8 cm; weight 72.9±19.3 kg. Measurements are taken at baseline, and after 1, 2, 3, 4, 5 and 6 hours after supplementation for each of the Go/No Go Test, the Vigilance Task Test, the Sternberg Task Test, and the Berg-Washington Card Sorting Task Test.

Figure 4:
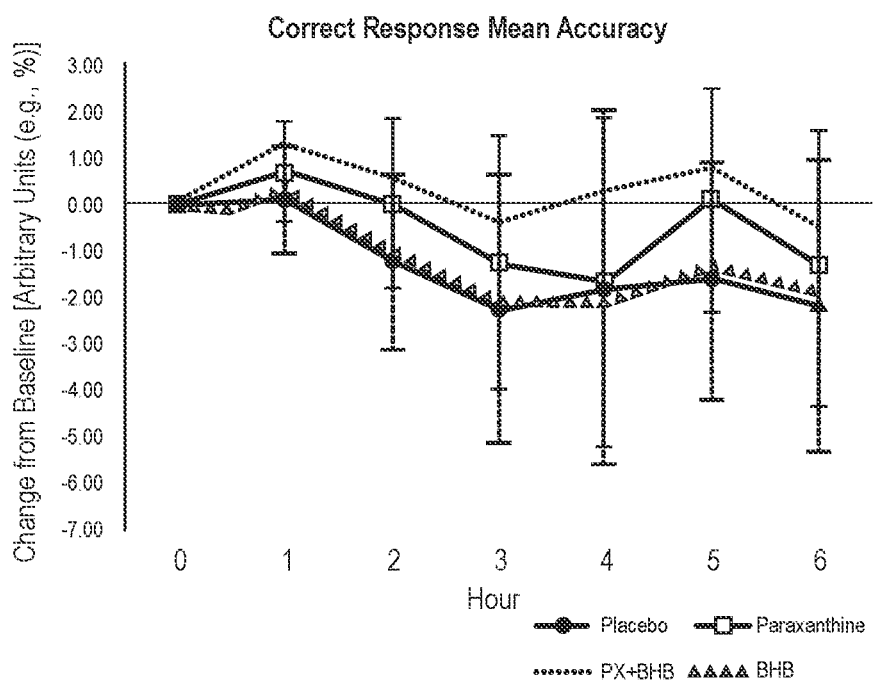
FIG. 4 illustrates expected results for a Go/No Go Attention and Inhibitory Control Test, showing incidence of correct responses, resulting from different respective treatments of paraxanthine in combination with BHB, paraxanthine alone, BHB alone, and a placebo, showing that improvement in the incidence of correct responses is expected to be greater with the combination treatment of paraxanthine+BHB by more than just the sum of the BHB only and paraxanthine only treatments.
Figure 5:
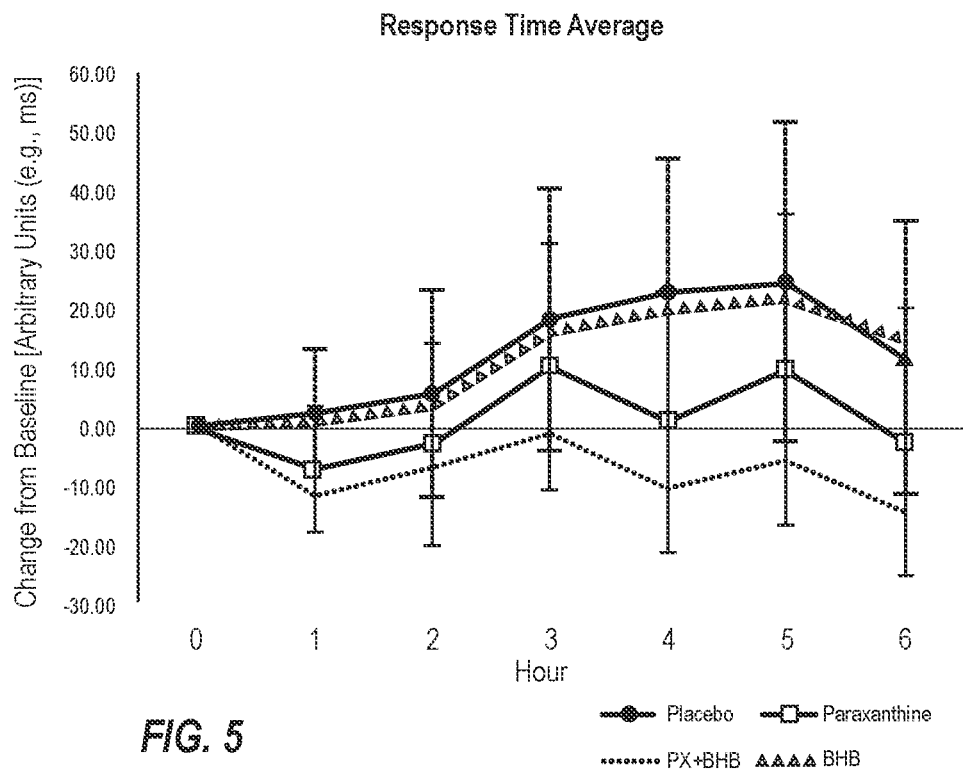
FIG. 5 illustrates expected results for a Go/No Go Attention and Inhibitory Control Test, showing expected average response time, resulting from different respective treatments of paraxanthine in combination with BHB, paraxanthine alone, BHB alone, and a placebo.

FIGS. 4 and 5 illustrate expected results of the Go/No Go Test. As shown, paraxanthine supplementation, particularly in combination with BHB, results in faster response times. The placebo, and BHB alone show a decrease in correct answers over time (see FIG. 4), indicating onset of mental fatigue. There is little separation between the charted response for the placebo as compared to BHB alone. Surprisingly, the combination of paraxanthine with BHB shows a significant, synergistic improvement in both correct response accuracy and average response time, as compared to paraxanthine alone. The combined use of paraxanthine with BHB provides synergistically increased capacity for sustained attention and response control, as shown by the results of the Go/No Go Test.

Figure 6:
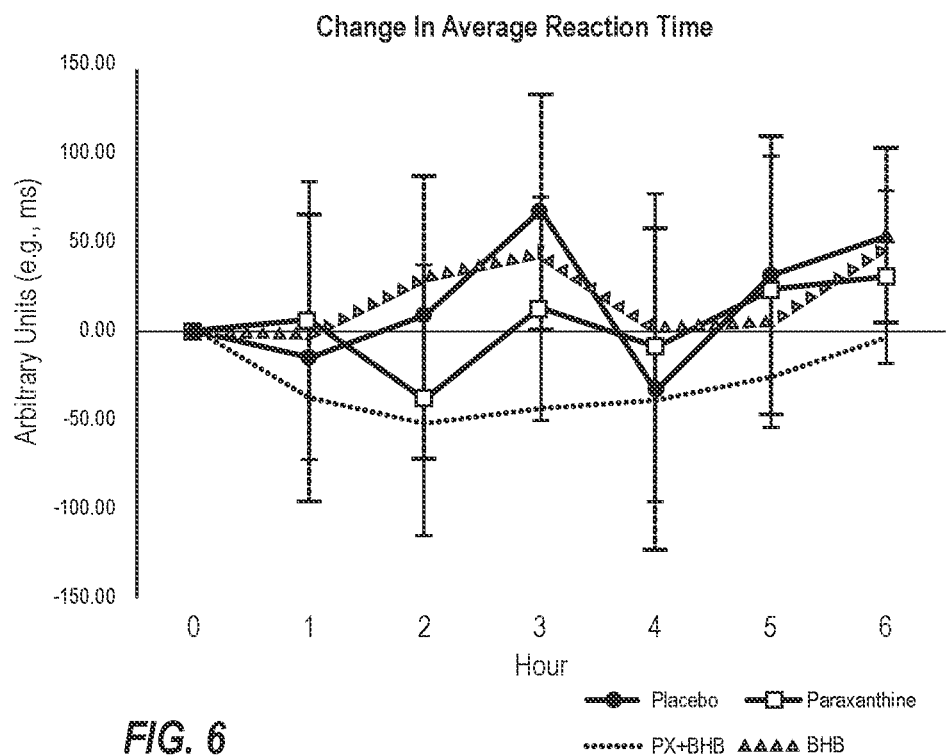
FIG. 6 illustrates expected results for a Vigilance Task Test, showing expected average response time, resulting from different respective treatments of paraxanthine in combination with BHB, as compared to paraxanthine alone, BHB alone, and a placebo.

FIG. 6 illustrates expected results of the Vigilance Task Test. As shown, paraxanthine supplementation, particularly in combination with BHB, results in faster response times. In contrast, the placebo, and BHB alone show significantly slower reaction times (e.g., particularly at 3 hours and 6 hours from the baseline). Surprisingly, the combination of paraxanthine with BHB shows a significant, synergistic improvement in average response time, as compared to paraxanthine alone. The combined use of paraxanthine with BHB provides synergistically increased capacity for sustained attention, as shown by the results of the Vigilance Task Test.

Figure 7:
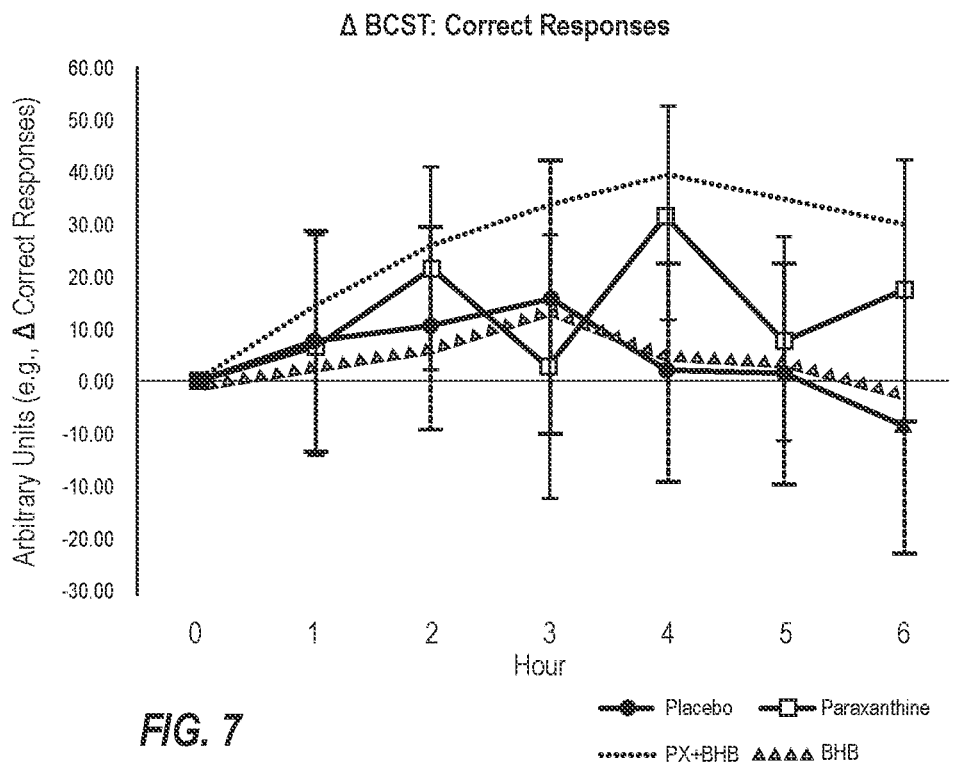
FIG. 7 illustrates expected results for a Berg-Washington Card Sorting Task Test, showing expected incidence of correct responses, resulting from different respective treatments of paraxanthine in combination with BHB, as compared to paraxanthine alone, BHB alone, and a placebo.
Figure 8:
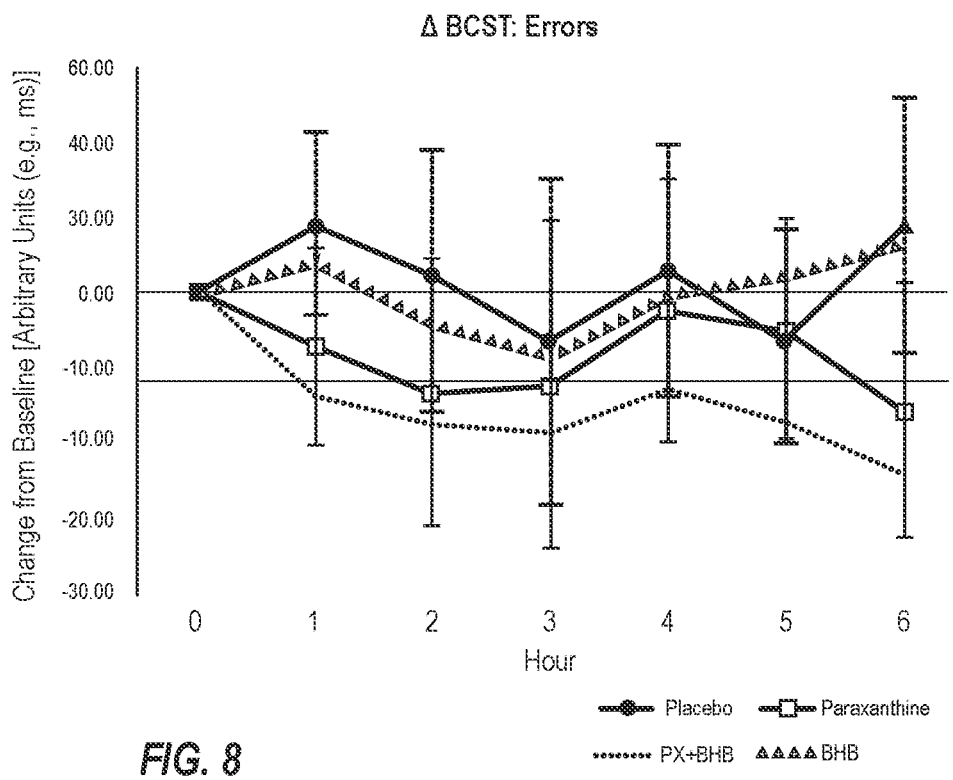
FIG. 8 illustrates expected results for a Berg-Washington Card Sorting Task Test, showing expected incidence of errors, resulting from different respective treatments of paraxanthine in combination with BHB, as compared to paraxanthine alone, BHB alone, and a placebo.

FIGS. 7-8 illustrate expected results of the Berg-Washington Card Sorting Task Test. As shown, paraxanthine supplementation, particularly in combination with BHB, results in a significant increase in the number of correct responses, and a reduction in the number of errors. While paraxanthine alone provides some such benefit, the increase in correct answers, and reduction in errors is surprisingly increased, by further supplementing with BHB in combination with paraxanthine. Such a combination of paraxanthine and BHB surprisingly and synergistically increases cognitive flexibility or the ability to set-shift between old versus new rule changes, as shown by the results of the Berg-Washington Card Sorting Task Test.

Figure 9:
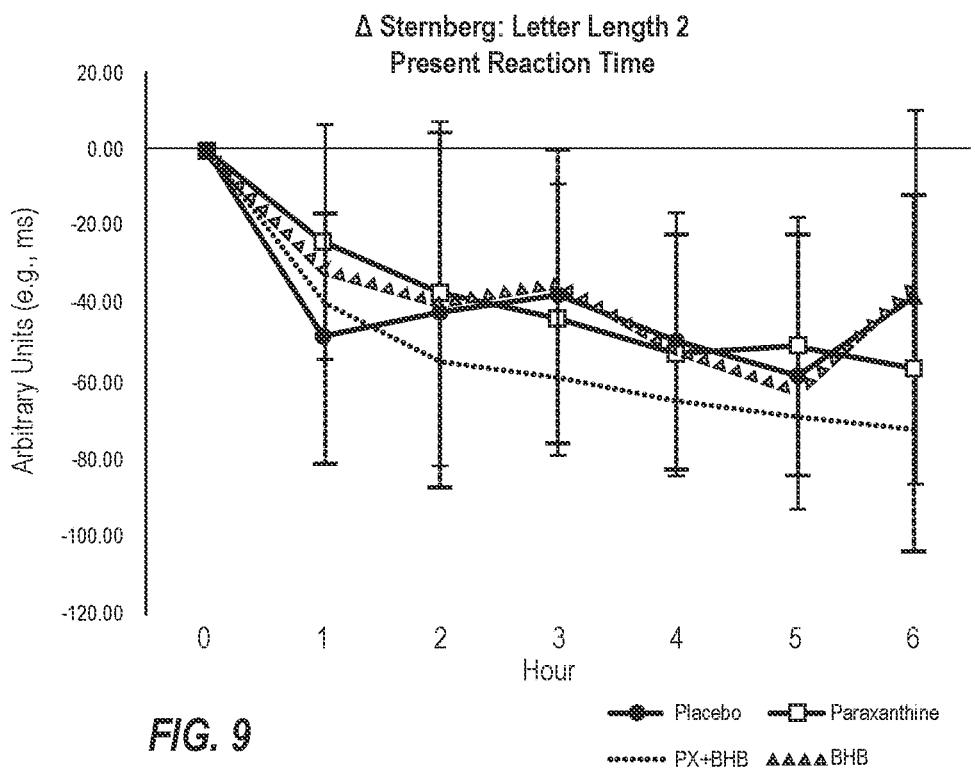
FIG. 9 illustrates expected results for a Sternberg Test with a letter length of 2, showing expected reaction time, resulting from different respective treatments of paraxanthine in combination with BHB, as compared to paraxanthine alone, BHB alone, and a placebo.
Figure 10:
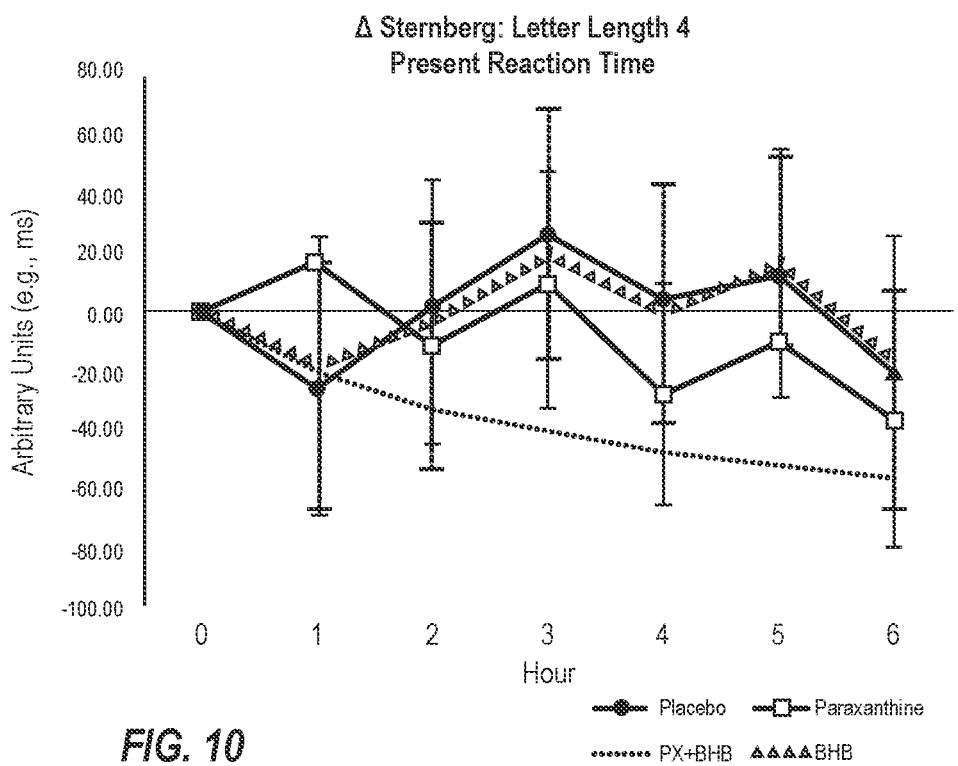
FIG. 10 illustrates expected results for a Sternberg Test with a letter length of 4, showing expected reaction time, resulting from different respective treatments of paraxanthine in combination with BHB, as compared to paraxanthine alone, BHB alone, and a placebo.
Figure 11:
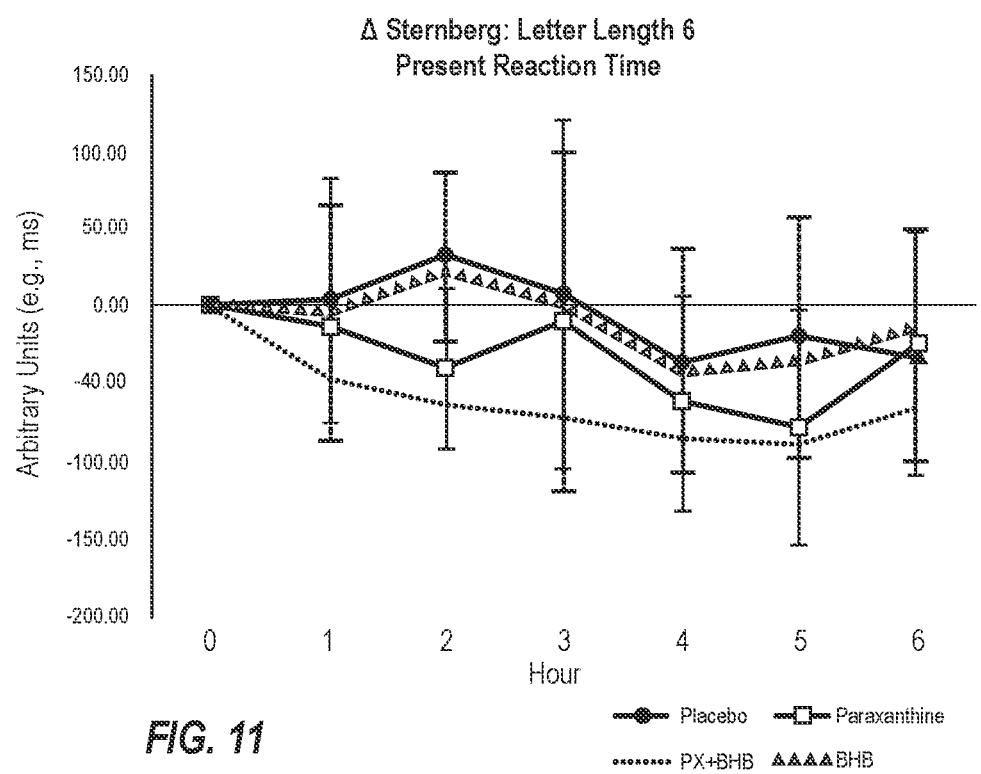
FIG. 11 illustrates expected results for a Sternberg Test with a letter length of 6, showing expected reaction time, resulting from different respective treatments of paraxanthine in combination with BHB, as compared to paraxanthine alone, BHB alone, and a placebo.

FIGS. 9-11 illustrate expected results of the Sternberg Test. As shown, paraxanthine supplementation, particularly in combination with BHB, results in a decreased mean response time, as compared to the placebo, or supplementation with BHB alone. While paraxanthine alone provides some reduction in reaction time, faster response times are surprisingly provided by supplementing with BHB in combination with paraxanthine. Such a combination of paraxanthine and BHB surprisingly and synergistically increases short term/working memory, particularly with longer letter lengths, as shown by the results of the Sternberg Test.

The key findings of the various cognitive tests is that acute paraxanthine and BHB supplementation improves cognition in all 3 aspects of executive function: cognitive flexibility, short term memory, and sustained attention. While cognition improvement is provided by paraxanthine supplementation alone, when combined with BHB, the improvements are surprisingly and synergistically enhanced. For example, BHB supplementation alone provides little if any significant benefit over the placebo, but when combined with paraxanthine, an improvement over the paraxanthine only results is achieved. Such results are surprising and unexpected, showing a synergy between the paraxanthine and the BHB.

Additional clinical studies are conducted to compare the effects achieved with paraxanthine, relative to caffeine. Participating subjects are dosed with 200 mg paraxanthine, 200 mg caffeine, 5 g BHB, 200 mg of paraxanthine+5 g BHB, 200 mg of caffeine+5 g BHB, 200 mg of paraxanthine+200 mg caffeine+5 g BHB, or placebo. The testing is conducted under double blind, placebo controlled conditions. The subjects include 12 healthy trained male runners, aged 26±5 years. Baseline cognition tests are administered (PRE), the given supplement is ingested, and after 60 minutes of rest, a pre-race cognition test (PRE-EX) is administered. A 10 km run on a treadmill is then performed, followed by a post-race cognition test (POST), The cognition tests include a Vigilance Task Test (measuring the ability to remain heedfully vigilant) and a Berg-Washington Card Sorting Task Test (measuring cognitive flexibility).

Figure 12A:
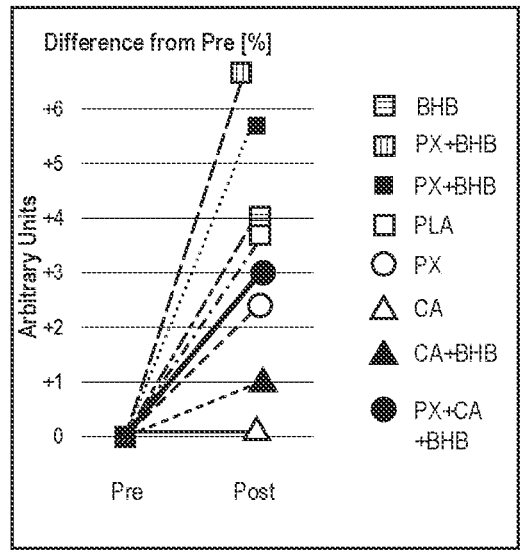
FIG. 12A illustrates expected results for a Berg-Washington Card Sorting Task Test, showing expected incidence of correct responses, resulting from different respective treatments of paraxanthine in combination with BHB, as compared to paraxanthine alone, BHB alone, caffeine and paraxanthine in combination with BHB, caffeine alone, caffeine in combination with BHB, and a placebo.
Figure 12B:
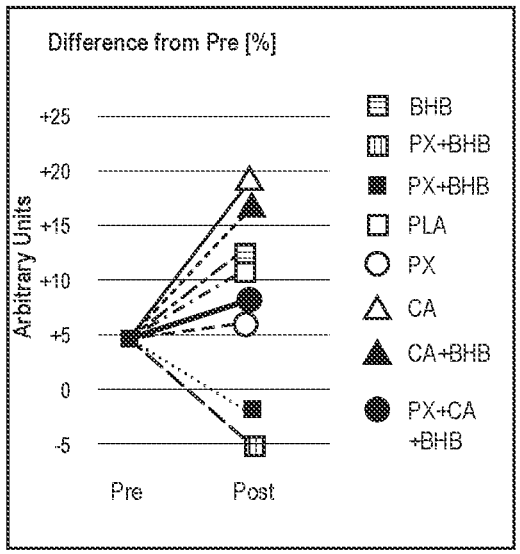
FIG. 12B illustrates expected results for a Berg-Washington Card Sorting Task Test, showing expected incidence of errors, resulting from different respective treatments of paraxanthine in combination with BHB, as compared to paraxanthine alone, BHB alone, caffeine and paraxanthine in combination with BHB, caffeine alone, caffeine in combination with BHB, and a placebo.
Figure 12C:
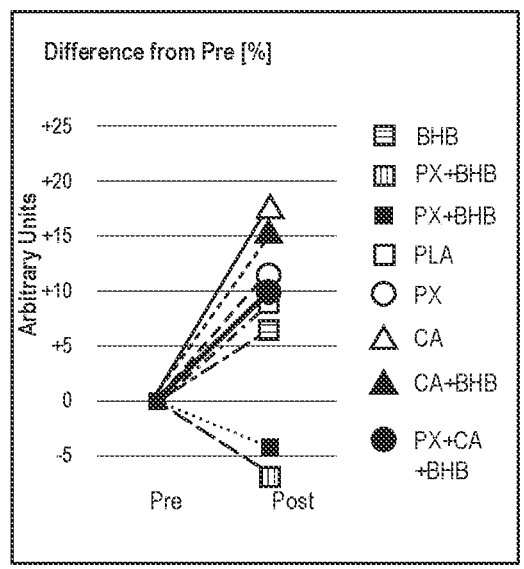
FIG. 12C illustrates expected results for a Berg-Washington Card Sorting Task Test, showing expected perseverative errors, resulting from different respective treatments of paraxanthine in combination with BHB, as compared to paraxanthine alone, BHB alone, caffeine and paraxanthine in combination with BHB, caffeine alone, caffeine in combination with BHB, and a placebo.
Figure 12D:
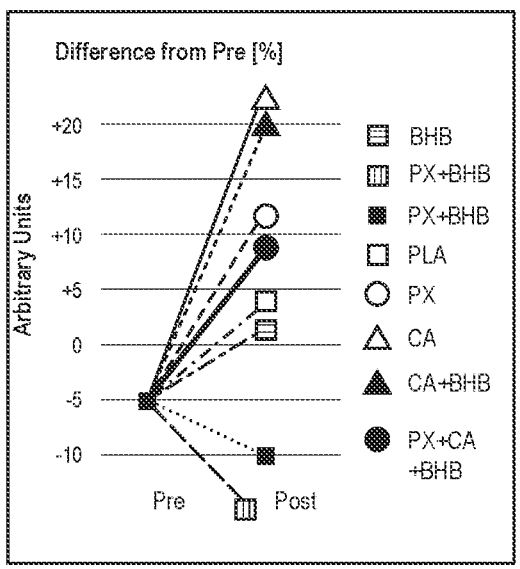
FIG. 12D illustrates expected results for a Berg-Washington Card Sorting Task Test, showing expected perserverative errors (PAR rules), resulting from different respective treatments of paraxanthine in combination with BHB, as compared to paraxanthine alone, BHB alone, caffeine and paraxanthine in combination with BHB, caffeine alone, caffeine in combination with BHB, and a placebo.

Expected results from such testing are shown in FIGS. 12A-12D, where FIG. 12A shows the difference in the incidence (e.g., percentage) of correct responses in the POST test, relative to the PRE test. FIG. 12B shows the difference in the incidence (e.g., percentage) of errors in the POST test, relative to the PRE test. FIG. 12C shows the difference in incidence (e.g., percentage) of perservative errors in the POST test relative to the PRE test. FIG. 12D shows the difference in incidence (e.g., percentage) of perserverative errors (PAR rules) in the POST test relative to the PRE test. While paraxanthine alone provides some improvement in correct responses and reduced errors, even further improved results are surprisingly provided by supplementing with BHB in combination with paraxanthine. Such a combination of paraxanthine and BHB surprisingly and synergistically increases clarity, vigilance, and cognitive flexibility, while reducing mental fatigue. Caffeine supplementation, even if combined with paraxanthine, and/or BHB, provides poor results, as shown. For example, all examples including caffeine result in decreases in correct responses, and an increase in errors, even compared to the placebo (i.e., a placebo, or no supplementation is better than any supplementation that includes caffeine). Thus, in an embodiment, the present compositions are substantially or entirely free of caffeine.

Figure 13:
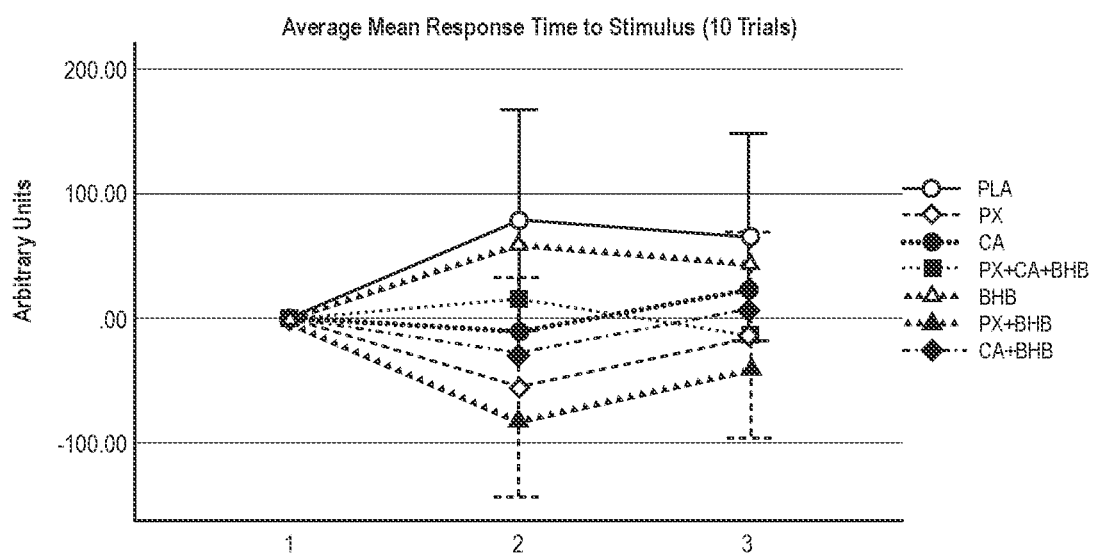
FIG. 13 illustrates expected results for a Vigilance Task Test, showing expected average response time, resulting from different respective treatments of paraxanthine in combination with BHB, as compared to paraxanthine alone, BHB alone, caffeine and paraxanthine in combination with BHB, caffeine alone, caffeine in combination with BHB, and a placebo.

FIG. 13 charts expected response times for a Vigilance Task Test, for the same supplementations shown in FIGS. 12A-12D. As shown, supplementation with paraxanthine alone provides some benefit, but an increased, synergistic benefit is provided when supplementing with paraxanthine+BHB. Supplements that include caffeine may decrease reaction time as shown, although not to the degree provided by supplements that are free of caffeine, and caffeine causes an increase in errors, as shown in FIGS. 12A-12D.

Such clinical studies show that paraxanthine supplementation, particularly in combination with BHB improve cognition PRE-EX, and especially POST-EX, that caffeine is detrimental, even in combination with paraxanthine and/or BHB.

Figure 14A:
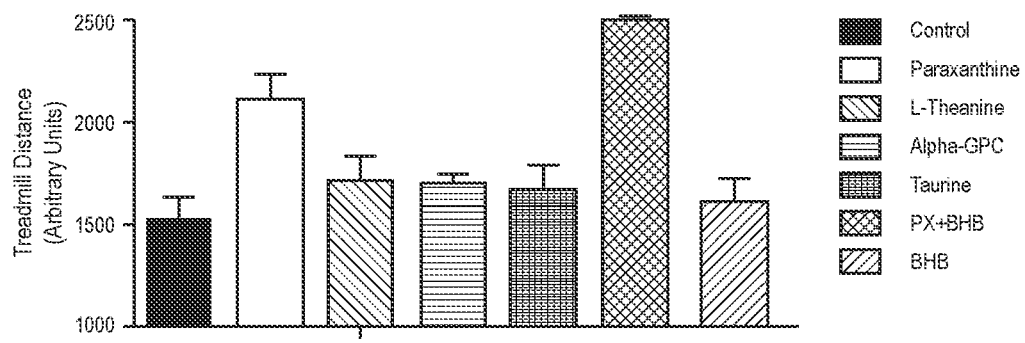
FIG. 14A-14C illustrate expected results for treadmill distance (14A), muscle mass (14B), and hand grip strength (14C), resulting from different respective treatments of paraxanthine in combination with BHB, as compared to paraxanthine alone, BHB alone, and various amino acids and amino acid derivatives.
Figure 14B:
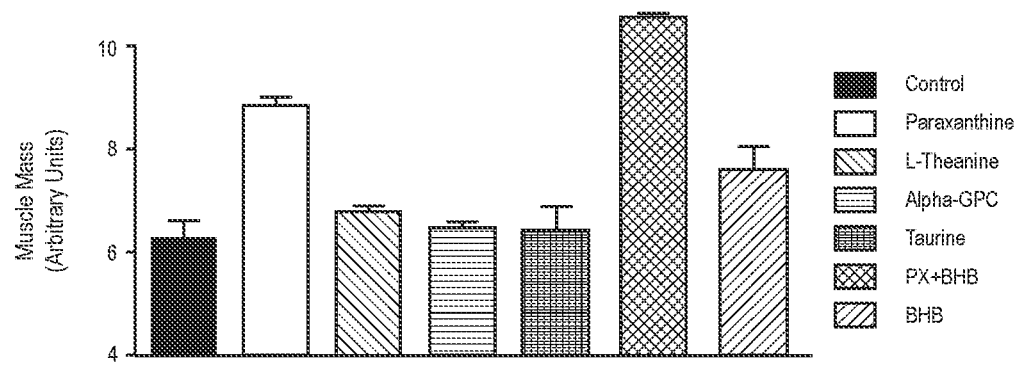
Figure 14C:
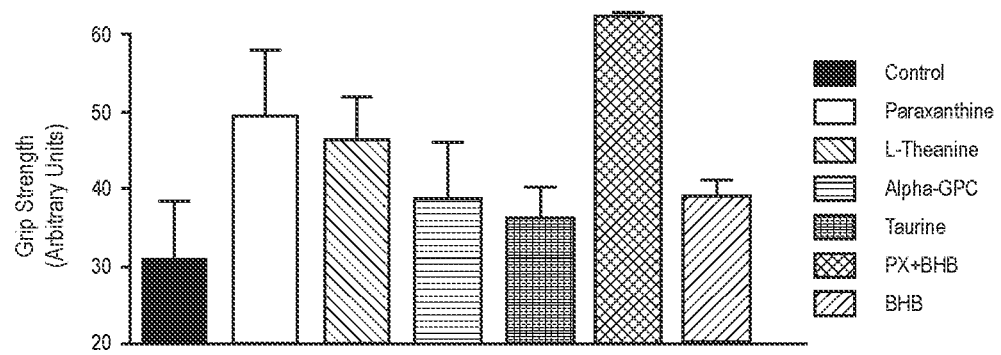

FIGS. 14A-14C show expected results of a 28-day sports nutrition clinical study, where participants are supplemented with paraxanthine alone (100 mg), BHB alone (5 g), paraxanthine (100 mg) in combination with BHB (5 g), or one of various muscle building supplements (e.g., L-theanine (50 mg), alpha-GPC (200 mg), or taurine (500 mg)). Participants exercise 5 days per week, of the 4-week study. While paraxanthine alone provides some improvement in muscle mass, endurance, and grip strength, even further improved results are surprisingly provided by supplementing with BHB in combination with paraxanthine. Such a combination of paraxanthine and BHB surprisingly and synergistically increases muscle mass, muscular endurance, and grip strength. Increases in nitric oxide levels, as well as improved blood lipids scores (e.g., TG, TC, LDL, HDL) are also observed.

In an age-related cognitive decline study, expected results show supplementation with paraxanthine in combination with BHB provides improved cognitive performance, improved neurotransmitter levels, improved brain protection, and improved oxidative stress, beyond that provided by paraxanthine alone, or BHB alone. Such expected results are shown in Table 2. As shown, BHB alone provides little if any benefit, as compared to the control. When paired with paraxanthine, the combination provides a synergistic decrease in escape latency and Amyloid Aβ1-40 concentration, while providing a synergistic increase in acetylcholine, dopamine, glutathione, catalase, and BDNF.

TABLE 2

|  | PX (25 mg) | PX (100 mg) | BHB (5 g) | PX + BHB (100 mg + 5 g) | Control |
| --- | --- | --- | --- | --- | --- |
| Escape Latency (s) | 49.9 | 21.31 | 50 | 15 | 53.02 |
| Acetylcholine (U/mL) | 61.04 | 69.27 | 58 | 80 | 58.65 |
| Dopamine (ng/L) | 493.65 | 596.32 | 475 | 700 | 474.3 |
| Glutathione (ug/mL | 24.04 | 34.41 | 22 | 40 | 21.85 |
| Catalase (U/mL) | 30.24 | 38.91 | 28 | 45 | 27.76 |
| BDNF (pg/mL) | 828.05 | 939.15 | 775 | 1050 | 775.04 |
| Amyloid Aβ1-40 (g/mL) | 280.42 | 216.66 | 295 | 175 | 295.09 |

In a Forced Swim and Cook's Pole Climbing Test on mice, expected results show supplementation with paraxanthine in combination with BHB provides improved duration of active swimming, and increased scores on the climbing test, beyond that provided by paraxanthine alone, BHB alone, or various other tested muscle building supplements (e.g., L-theanine, alpha-GPC, and taurine). Such expected results are shown in Table 3. As shown, BHB alone provides little if any benefit, as compared to the control. When paired with paraxanthine, the combination provides a synergistic decrease in duration of immobility and No. of Climbing in Cook's Pole Climbing Test, while providing a synergistic increase in duration of mobility/active swimming.

TABLE 3

|  | Duration of Immobility (min) | Duration of mobility/active swimming (min) | No. of Climbing |
| --- | --- | --- | --- |
| PX (100 mg) | 5.85 | 24.15 | 2.75 |
| BHB (5 g) | 9.5 | 20 | 6 |
| PX + BHB (100 mg + 5 g) | 4 | 27 | 2.2 |
| L-Theanine (50 mg) | 8.74 | 21.26 | 4.38 |
| Alpha-GPC (200 mg) | 9.38 | 20.63 | 5.5 |
| Taurine (500 mg) | 9.61 | 20.39 | 6.5 |
| Control | 10.3 | 19.7 | 7.13 |

Figure 15A:
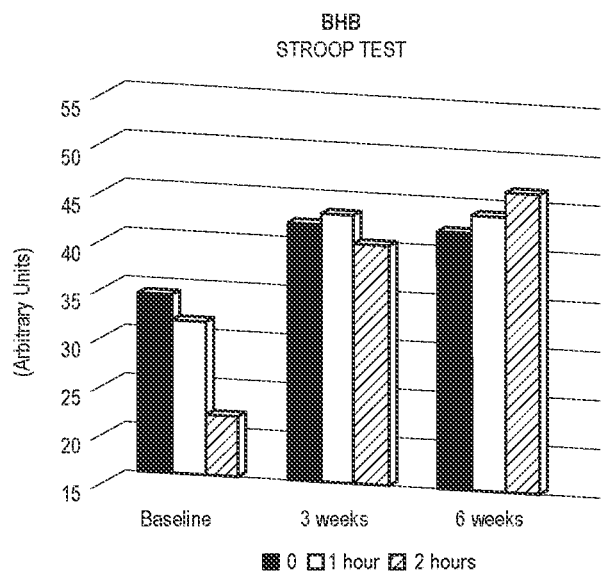
FIGS. 15A-15C illustrate expected results for a Stroop Test, resulting from different respective treatments of paraxanthine in combination with BHB, as compared to paraxanthine alone, and BHB alone, over a 6 week period.
Figure 15B:
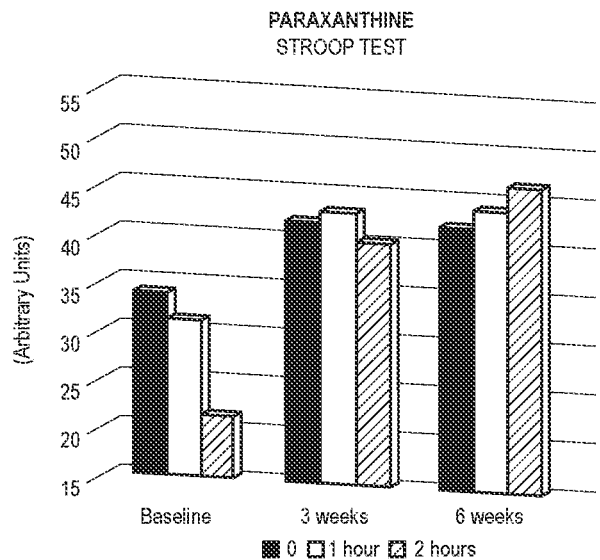
Figure 15C:
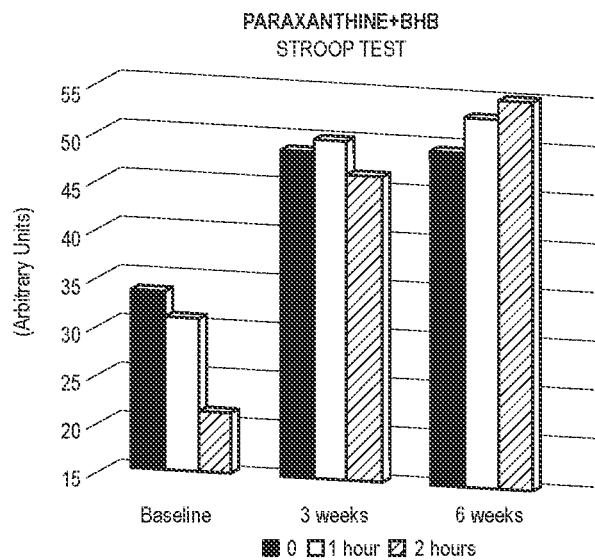

FIGS. 15A-15C show expected results of a clinical Stroop Test study, where participants are supplemented with paraxanthine alone (200 mg), BHB alone (5 g), or paraxanthine (200 mg) in combination with BHB (5 g) over a 6-week period. The Stroop effect refers to the delay in reaction time between congruent and incongruent stimuli. The Stroop Test is a well-known psychological test which demonstrates this effect, when there is a mismatch between the name of a color (e.g., "blue", "green", or "red") and the color in which it is printed (i.e., the word "red" is printed in blue ink instead of red ink). When asked to name the color of the word a subject takes longer and is more prone to make an error when the color of the ink does not match the name of the color. While paraxanthine alone (FIG. 15B) provides some improvement in reaction speed and number or correct answers in such a Stroop test, even further improved results are surprisingly provided by supplementing with BHB in combination with paraxanthine (FIG. 15C). As shown in FIG. 15A, BHB alone provides little if any benefit, as compared to the baseline (before supplementation). When paired with paraxanthine, the combination provides a synergistic improvement in mental acuity.

Figure 16:
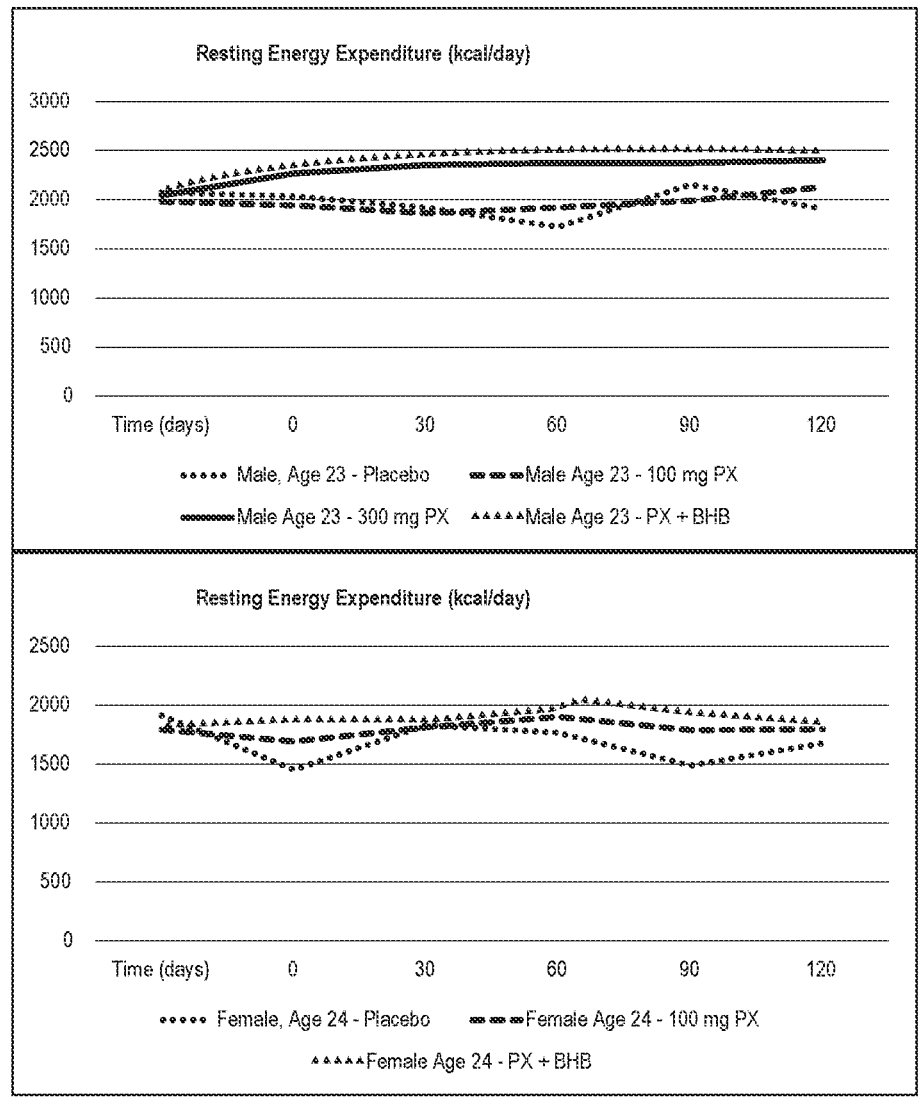
FIG. 16 illustrates expected results for Resting Energy Expenditure, resulting from different respective treatments of paraxanthine in combination with BHB, as compared to paraxanthine alone, BHB alone, and a placebo.

FIGS. 16A-16B show expected results of a clinical Resting Energy Expenditure study, where participants are supplemented with paraxanthine alone (100 mg or 300 mg), BHB alone (5 g), or paraxanthine (100 mg or 300 mg) in combination with BHB (5 g) over a 180-day period. While paraxanthine alone provides some increase in resting energy expenditure (which is helpful for weight loss), even further improved results are surprisingly provided by supplementing with BHB in combination with paraxanthine. As shown, BHB alone provides only a minor benefit. However, when paired with paraxanthine, the combination provides a synergistic increase in resting metabolic energy expenditure. Because of the presence of the BHB ketone body component, such increased metabolic rate is also more likely to occur within the context of ketogenic state, where fat is principally used as the caloric energy source for the increased resting metabolic rate.

IV. Dosage Forms and Administration

Compositions described herein may be provided in various forms, such as one-part or multi-part compositions configured for administration by one or more of ingestion, intragastric, injection, topical application, inhalation, oral mucosal administration, rectal administration, vaginal administration, or parenteral administration.

Non-limiting examples of the foregoing administration routes include, but are not limited to, ingestible compositions, suppositories (anal or vaginal), transdermal patch, sublingual compositions, subdermal modalities, solid, powder, liquid, gel, tablet, capsule, other dietetically or pharmaceutically acceptable form, vaporizable cartridge, nebulizing liquid, smokable bolus, syringe for intravenous injection, nasal spray or vapor, inhalable pulmonary composition, enema, douche, injectable bolus, subdermal implant (e.g., pellet or stick), and the like.

Inhalation can be performed using a heat vaporizer (e.g., vape stick, mod box, e-cigarette, or vape cartridge), smoking a bolus (e.g., using a pipe, water pipe, bong, rolling papers, glass pipe, chillum, one-hitter, hookah, apple pipe, avocado pipe, gas mask, snorkel gear,), or a nebulizer.

Edibles include drinks, soda, energy shots, sparkling water, beer, wine, spirits, hard seltzer, coconut water, fruit juices, chocolate, fruit chews, oral drops, coconut oil, butter, water, milk, cookies, cake, ice cream, gummy bears, pizza crust, brownies, pastries, yogurt, frozen yogurt, chewable vitamins, candy, protein powder, supplements, supplement powders, consumable powders, coffee, tea, and the like.

Oral/concentrates/extractions include chewing gum, tinctures, oils, sublingual sprays, pills, capsules, quick-dissolve tablets, troches, nasal sprays, eyedrops, dabs, shatter, and rosin.

Topicals include lotions, creams, salves, balms, transdermal patches, gels, shampoo, conditioner, deodorant, lip balm, lipstick, and makeup.

Solid or powder compositions may include one or more additional components configured to lower the hygroscopicity of the composition. For example, various anticaking agents, flow agents, and/or moisture absorbers, in types and amounts that are safe for consumption, may be included. Such additional components may include one or more of an aluminosilicate, ferrocyanide, carbonate or bicarbonate salt, silicate (e.g., sodium or calcium silicate), phosphate salt (e.g., tricalcium phosphate), talcum, powdered cellulose, and the like.

In alternative embodiments, the Paraxanthine-BHB composition may be provided as a liquid, such as in the form of a shot or mouth spray for fast delivery and absorption, or as a gel. Liquid or gel forms may include one or more carriers, such as water, ethanol, glycerin, propylene glycol, 1,3-propandiol, and the like, into which the components are dissolved or dispersed. The composition may include flavoring agents that help mask the somewhat poor taste of BHB compounds. These flavoring agents may include essential oils, such as peppermint, natural and artificial sweeteners, and other flavorants known in the art.

The Paraxanthine-BHB composition may include one or more supplements known in the art, such as vitamins, minerals or herbs. In an embodiment, little if any caffeine is present, as caffeine interferes with the efficacy of the paraxanthine, as shown above. For example, if present, caffeine may be present at less than 10 mg, less than 5 mg, less than 3 mg, or less than 1 mg. The compositions may advantageously be substantially free or entirely free of caffeine.

The Paraxanthine-BHB compositions described herein may be provided within a dosage regimen effective in inducing and sustaining ketosis and/or providing other benefits described herein. For example, the mass of exogenous ketone bodies (e.g., BHB) in a daily dose (for an average adult of about 175 lbs.) may range from about 0.5 gram to about 50 grams, or about 1 gram to about 40 grams, or about 2 grams to about 30 grams, or about 3 grams to about 25 grams, or about 4 grams to about 20 grams, and may be provided using one or more unit doses. The mass of the paraxanthine component in a daily dose (for an average adult of about 175 lbs.) may range from about 25 mg to about 1000 mg, about 50 mg to about 500 mg, about 75 mg to about 400 mg, about 100 mg to about 300 mg, or about 125 mg to about 250 mg. As needed, dosages may be adjusted (e.g., linearly) based on weight of the subject. The paraxanthine component and the BHB ketone body component may be mixed/combined, though some methods may provide the components separately. The daily dose(s) may be taken as a single daily dose or as multiple doses (e.g., 2, 3, or 4 times daily).

In some embodiments, the composition includes a ratio of the BHB ketone body component to the paraxanthine component in a range of about 1:1 to about 500:1, though it is preferable that the amount of the BHB ketone body component is greater, and preferably significantly greater than the paraxanthine component. For example, a more preferable ratio of the BHB ketone body component to the paraxanthine component may range from about 5:1 to about 300:1 from about 5:1 to about 100:1, or from about 5:1 to about 50:1. The BHB component is present at significantly higher amounts, as it is provided as a caloric energy source, while the paraxanthine is provided for other purposes (e.g., enhancement of cognitive flexibility, increased sustained attention, improved working memory, increased inhibitory control, neuroprotection, etc.). Example weight ratios of the BHB ketone body component(s) to paraxanthine component(s) include 3:1, 5:1, 10:1, 15:1, 20:1, 25:1, 30:1, 40:1, 50:1, 75:1, 100:1, 200:1, 300:1, 400:1 and 500:1, and any range with any of the foregoing as endpoints. These and other ratios disclosed herein will generally apply when using 1,3-butanediol in addition to or in place of BHB.

In a preferred embodiment, a Paraxanthine-BHB composition is administered in one or more unit doses per day via oral administration of the composition in a solid, powdered form or liquid, such as in a powdered mixture (e.g., powder filled gelatin capsules), hard-pressed tablets, or other oral administration route known to those skilled in the art.

In some embodiments, multiple doses of the composition are administered. The frequency of administration of the composition can vary depending on any of a variety of factors, such as timing of treatment from previous treatments, objectives of the treatment, and the like. The duration of administration of the composition (e.g., the period of time over which the agent is administered), can vary depending on any of a variety of factors, including subject response, desired effect of treatment, etcetera.

The amount of the composition to be administered can vary according to factors such as the degree of susceptibility of the individual, the age, sex, and weight of the individual, idiosyncratic responses of the individual, and the like. The "therapeutically effective amount" is that amount necessary to promote a therapeutically effective result in vivo. In accordance with the present disclosure, a suitable single dose size is a dose that is capable of preventing or alleviating (reducing or eliminating) a symptom in a patient when administered one or more times over a suitable time period (e.g., a daily dose).

The amount of composition administered will depend on potency, absorption, distribution, metabolism, and excretion rates of the composition components, the method of administration, and the particular disorder being treated, as well as other factors known to those of skill in the art. The dose should be sufficient to affect a desirable response, such as a therapeutic or prophylactic response against a particular disorder or condition, taking into account the severity of the condition to be alleviated. The compounds may be administered once over a given time period (e.g., once per day), or may be divided and administered over intervals of time. It is to be understood that administration may be adjusted according to individual need and professional judgment of a person administrating or supervising the administration of the compositions.

VII. Examples

The following is a description of exemplary Paraxanthine-BHB compositions useful for enhancing cognitive flexibility, sustained attention, working memory, inhibitory control, and neuroprotection in a subject.

Example 1

A paraxanthine-BHB composition is prepared by mixing a BHB ketone body component comprising one or more of sodium beta-hydroxybutyrate, potassium beta-hydroxybutyrate, magnesium beta-hydroxybutyrate, or calcium beta-hydroxybutyrate with a paraxanthine component. The weight ratio of the BHB ketone body component to paraxanthine is 5:1. The Paraxanthine-BHB composition is in a form that is readily administered, such as in powder form as a dietary supplement mixed with food or drink, in the form of one or more capsules or tablets, or in liquid form such as a mouth spray, liquid shot, or beverage. The Paraxanthine-BHB composition provides superior results compared to a composition containing caffeine and BHB.

Example 2

A paraxanthine-BHB composition is prepared by mixing a BHB ketone body component comprising one or more of sodium beta-hydroxybutyrate, potassium beta-hydroxybutyrate, magnesium beta-hydroxybutyrate, or calcium beta-hydroxybutyrate with a paraxanthine component. The weight ratio of the BHB ketone body component to paraxanthine is 25:1. The Paraxanthine-BHB composition is in a form that is readily administered, such as in powder form as a dietary supplement mixed with food or drink, in the form of one or more capsules or tablets, or in liquid form such as a mouth spray, liquid shot, or beverage. The Paraxanthine-BHB composition provides superior results compared to a composition containing caffeine and BHB.

Example 3

A paraxanthine-BHB composition is prepared by mixing a BHB ketone body component comprising one or more of sodium beta-hydroxybutyrate, potassium beta-hydroxybutyrate, magnesium beta-hydroxybutyrate, or calcium beta-hydroxybutyrate with a paraxanthine component. The weight ratio of the BHB ketone body component to paraxanthine is 100:1. The Paraxanthine-BHB composition is in a form that is readily administered, such as in powder form as a dietary supplement mixed with food or drink, in the form of one or more capsules or tablets, or in liquid form such as a mouth spray, liquid shot, or beverage. The Paraxanthine-BHB composition provides superior results compared to a composition containing caffeine and BHB.

Example 4

Any of the foregoing Examples is modified by substituting a portion of the beta-hydroxybutyrate salts(s) with beta-hydroxybutyric acid.

Example 5

Any of the foregoing Examples is modified by including one or more esters of beta-hydroxybutyrate.

Example 6

Any of the foregoing Examples is modified by supplementing or substituting at least a portion of the BHB with 1,3-butanediol.

Example 7

Any of the foregoing Examples is modified by substituting part of the beta-hydroxybutyrate salt(s) with one or more of sodium acetoacetate, potassium acetoacetate, magnesium acetoacetate, or calcium acetoacetate.

Example 8

Example 6 is modified by substituting a portion of the acetoacetate salt(s) with acetoacetic acid.

Example 9

Any of the foregoing Examples is modified by being in a dosage form that provides from about 0.5 gram to about 50 grams, or about 1 gram to about 40 grams, or about 2 grams to about 30 grams, or about 3 grams to about 25 grams, or about 4 grams to about 20 grams, of the BHB ketone body component.

Example 10

Any of the foregoing Examples is modified by being in a dosage form that provides from about 50 mg to about 500 mg, or about 50 mg to about 400 mg, or about 100 mg to about 300 mg, of the paraxanthine component.

Example 11

Any of the foregoing Examples is modified by including one or more supplements, including one or more of vitamin (s), mineral(s) or herb(s).

Example 12

Any of the foregoing Examples is modified to include a liquid carrier comprising one or more of water, ethanol, glycerin, propylene glycol, or 1,3-propandiol.

Example 13

Any of the foregoing Examples is modified to further include a ketone body precursor selected from 1,3-butanediol, fatty acids, and/or esters of fatty acids, such as one or more medium chain fatty acids or one or more medium chain triglycerides (MCT).

Example 14

Any of the foregoing Examples is modified to include a short-chain fatty acid or ester thereof.

Example 15

Any of the foregoing Examples is modified by combining the composition with one or more fat burner supplements such as green tea, green tea extract (e.g., a composition including one or more isolated green tea catechins such as epigallocatechin gallate (EGCG)), green coffee extract, conjugated linoleic acid (CLA), tetradecyl thioacetic acid (TTA), *Coleus forskohlii* (i.e., forskolin), yohimbine, rauwolscine, capsaicin, raspberry ketones (e.g., 4-(4-hydroxyphenyl) butan-2-one, p-hydroxybenzyl acetone), ephedrine, synephrine (e.g., bitter orange extract), octopamine, 1,3-dimethylamylamine, higenamine, fucoxanthin, acetylcholine modulators, nicotine, coca leaf derivative, ursolic acid, clenbuterol, noradrenaline reuptake inhibitors (e.g., hordenine, atomoxetine), 7-oxodehydroepiandrosterone (i.e., 7-keto DHEA), thyroid hormones (e.g., triiodothyronine), or combinations thereof. The resulting composition is expected to provide greater lipolysis and/or fat oxidation effects.

Example 16

Any of the foregoing Examples is modified by combining the composition with one or more nootropic supplements such as tyrosine, L-DOPA (i.e., L-3,4-dihydroxyphenylalanine), tryptophan, and 5-hydroxytryptophan (5-HTP), racetams such as such as piracetam, oxiracetam, and aniracetam, L-theanine, D-serine, phosphatidylserine, tolcapone, uridine, vinpocetine, norepinephrine reuptake inhibitors such as hordenine and atomoxetine, *Panax ginseng, Ginkgo* biloba, *Rhodiola rosea*, *Polygala tenuifolia*, *Muira puama*, *Eschscholzia californica*, *Convolvulus pluricaulis*, *Centella asiatica*, *Evolvulus alsinoides*, *Bacopa monnieri*, *Epimedium* herbs, *Ashwagandha* herbs, cyclic adenosine monophosphate (cAMP) modulators such as forskolin, stimulants such as nicotine and amphetamines, cholinergic compounds and/or acetylcholine modulators such as huperzine-A, dimethylaminoethanol, choline, and alpha-glycerophosphocholine, and combinations thereof. The resulting combined supplement is expected to provide greater cognition, alertness, and/or mood effects.

Example 17

Any of the foregoing Examples is modified by including pharmaceutically or dietetically acceptable carrier.

Example 18

Any of the foregoing Examples is modified by being in a dosage form configured for administering by one or more of ingestion, intragastric, injection, topical, inhalation, oral mucosal, rectal, vaginal, or parenteral.

Unless otherwise stated, all percentages, ratios, parts, and amounts used and described herein are by weight.

Numbers, percentages, ratios, or other values stated herein may include that value, and also other values that are about or approximately the stated value, as would be appreciated by one of ordinary skill in the art. As such, all numeric values may be optionally modified by including the term "about" in a claim. Such values may thus include an amount or state close to the stated amount or state that still performs a desired function or achieves a desired result. A stated value should therefore be interpreted broadly enough to encompass values that are at least close enough to the stated value to perform a desired function or achieve a desired result, and/or values that round to the stated value. The stated values include at least the variation to be expected in a typical manufacturing or other process, and may include values that are within 10%, within 5%, within 1%, etc. of a stated value.

The phrase "substantially free of" or similar phrases as used herein means that the composition or article preferably comprises 0% of the stated component, although it will be appreciated that very small concentrations may possibly be present, e.g., through incidental formation, contamination, or even by intentional addition. Such components may be present, if at all, in amounts of less than 1%, less than 0.5%, less than 0.25%, less than 0.1%, less than 0.05%, less than 0.01%, less than 0.005%, less than 0.001%, or less than 0.0001%. In some embodiments, the compositions or articles described herein may be free or substantially free from any specific components not mentioned within this specification. For example, if present, caffeine may be present at less than 10 mg, less than 5 mg, less than 3 mg, or less than 1 mg in a provided dose of the Paraxanthine-BHB supplement.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A synergistic composition comprising:
   paraxanthine; and
   at least one ketone body or ketone body precursor selection from the group consisting of beta-hydroxybutyrate (BHB) salt, BHB ester, beta-hydroxybutyric acid, 1,3-butanediol, and combinations thereof,
   wherein the composition is in a dosage form that provides from about 0.5 gram to about 50 grams of the ketone body or ketone body precursor and about 50 mg to about 500 mg of the paraxanthine.

2. The synergistic composition of claim 1, wherein the composition comprises at least one of a BHB salt, BHB ester, or beta-hydroxybutyric acid.

3. The synergistic composition of claim 1, wherein the composition comprises 1,3-butanediol.

4. The synergistic composition of claim 1, wherein the composition further comprises at least one medium chain fatty acid or ester thereof.

5. The synergistic composition of claim 1, wherein the composition further comprises at least one short chain fatty acid or ester thereof.

6. The synergistic composition of claim 1, wherein the composition comprises a mixed salt comprising a plurality of cations selected from the group consisting of lithium ions, sodium ions, potassium ions, magnesium ions, calcium ions, and amino acid cations in combination with BHB anions.

7. The synergistic composition of claim 1, wherein the composition is provided in solid, powder, or liquid form.

8. The synergistic composition of claim 1, wherein the dosage form provides about 1 gram to about 40 grams, or about 2 grams to about 30 grams, or about 3 grams to about 25 grams, or about 4 grams to about 20 grams, of the ketone body or ketone body precursor.

9. The synergistic composition of claim 1, wherein the dosage form provides about 75 mg to about 400 mg, or about 100 mg to about 300 mg, of the paraxanthine.

10. The synergistic composition of claim 1, further comprising a pharmaceutically or dietetically acceptable carrier.

11. The synergistic composition of claim 1, wherein the composition provides one or more benefits selected from homeostasis promotion, neuroprotection, brain protection, memory enhancement, enhanced focus and clarity, improved cognitive performance, improved working memory, improved neurotransmitter levels, reduced oxidative stress, enhanced inhibitory control (ability to control attention), anxiolytic effect, reduced jitters, anti-depressant effect, anti-inflammatory effect, analgesic effect, suppression of depressive symptoms, cardiovascular benefits, blood pressure modulation, heart rate modulation, modulation of lethargy/lightheadedness associated with hypoglycemia upon entering a ketogenic state, moderation of the down-regulation of metabolic rate upon entering a ketogenic state, anti-aging, and reduced energy crash.

12. A synergistic composition comprising:
    paraxanthine; and
    and at least one ketone body precursor comprising 1,3-butanediol,
    wherein the composition is in a dosage form that provides from about 0.5 gram to about 50 grams of the ketone body precursor and about 50 mg to about 500 mg of the paraxanthine.

13. The synergistic composition of claim 12, wherein the composition further comprises at least one short chain fatty acid or ester thereof and/or at least one medium chain fatty acid or ester thereof.

14. The synergistic composition of claim 12, wherein the composition is provided in solid, powder, or liquid form.

15. The synergistic composition of claim 12, wherein the dosage form provides about 1 gram to about 40 grams, or about 2 grams to about 30 grams, or about 3 grams to about 25 grams, or about 4 grams to about 20 grams, of the ketone body precursor.

16. The synergistic composition of claim 12, wherein the dosage form provides about 75 mg to about 400 mg, or about 100 mg to about 300 mg, of the paraxanthine.

17. The synergistic composition of claim 12, further comprising a pharmaceutically or dietetically acceptable carrier.

18. The synergistic composition of claim 12, wherein the composition provides one or more benefits selected from homeostasis promotion, neuroprotection, brain protection, memory enhancement, enhanced focus and clarity, improved cognitive performance, improved working memory, improved neurotransmitter levels, reduced oxidative stress, enhanced inhibitory control (ability to control attention), anxiolytic effect, reduced jitters, anti-depressant effect, anti-inflammatory effect, analgesic effect, suppression of depressive symptoms, cardiovascular benefits, blood pressure modulation, heart rate modulation, modulation of lethargy/lightheadedness associated with hypoglycemia upon entering a ketogenic state, moderation of the down-regulation of metabolic rate upon entering a ketogenic state, anti-aging, and reduced energy crash.

19. A synergistic composition comprising:
paraxanthine; and
at least one ketone body or ketone body precursor selection from the group consisting of beta-hydroxybutyrate (BHB) salt, BHB ester, beta-hydroxybutyric acid, or 1,3-butanediol, and
a pharmaceutically or dietetically acceptable carrier,
wherein the composition is provided in solid, powder, or liquid form,
wherein the composition is in a dosage form that provides from about 0.5 gram to about 50 grams of the ketone body or ketone body precursor and about 50 mg to about 500 mg of the paraxanthine.

20. The synergistic composition of claim 19, wherein the composition provides one or more benefits selected from homeostasis promotion, neuroprotection, brain protection, memory enhancement, enhanced focus and clarity, improved cognitive performance, improved working memory, improved neurotransmitter levels, reduced oxidative stress, enhanced inhibitory control (ability to control attention), anxiolytic effect, reduced jitters, anti-depressant effect, anti-inflammatory effect, analgesic effect, suppression of depressive symptoms, cardiovascular benefits, blood pressure modulation, heart rate modulation, modulation of lethargy/lightheadedness associated with hypoglycemia upon entering a ketogenic state, moderation of the down-regulation of metabolic rate upon entering a ketogenic state, anti-aging, and reduced energy crash.

* * * * *